United States Patent
Hammerslag et al.

(10) Patent No.: US 10,433,999 B2
(45) Date of Patent: Oct. 8, 2019

(54) CLOSURE SYSTEM FOR BRACES, PROTECTIVE WEAR AND SIMILAR ARTICLES

(75) Inventors: Gary R. Hammerslag, Steamboat Springs, CO (US); James Capra, Steamboat Springs, CO (US)

(73) Assignee: Boa Technology, Inc., Denver, CO (US)

( * ) Notice: Subject to any disclaimer, the term of this patent is extended or adjusted under 35 U.S.C. 154(b) by 1026 days.

(21) Appl. No.: 13/614,647

(22) Filed: Sep. 13, 2012

(65) Prior Publication Data

US 2013/0012856 A1 Jan. 10, 2013

Related U.S. Application Data

(63) Continuation of application No. 11/854,522, filed on Sep. 12, 2007, now Pat. No. 8,277,401.
(Continued)

(51) Int. Cl.
*A61F 5/00* (2006.01)
*A61F 5/01* (2006.01)
(Continued)

(52) U.S. Cl.
CPC ............... *A61F 5/01* (2013.01); *A43C 11/14* (2013.01); *A43C 11/16* (2013.01); *Y10T 24/37* (2015.01)

(58) Field of Classification Search
CPC .... A61F 5/0585; A61F 5/05841; A61F 5/058; A61F 5/01; A61F 5/0111; A61F 5/0106; A61F 5/0123; A43C 11/14; A43C 11/1493; A43C 11/00; A43C 11/165; A43C 7/00; A43C 7/005; A43C 7/08; Y10T 24/37; Y10T 24/2183; Y10T 24/2187
(Continued)

(56) References Cited

U.S. PATENT DOCUMENTS 59,332 A 10/1866 White et al.
80,834 A 8/1868 Prussia
(Continued)

FOREIGN PATENT DOCUMENTS

AT 127075 2/1932
AT 244804 1/1966
(Continued)

OTHER PUBLICATIONS

U.S. Appl. No 09/056,601, filed Sep. 18, 2001, Gary R. Hammerslag.
(Continued)

*Primary Examiner* — Victoria J Hicks
(74) *Attorney, Agent, or Firm* — Kilpatrick Townsend & Stockton, LLP

(57) ABSTRACT

A closure system for braces, protective wear and similar articles is disclosed. The closure system includes a plurality of opposing lace guide members and a tightening mechanism. The closure system further includes a lace extending through the guide members and coupled to the tightening mechanism. In some embodiments, a quick release apparatus is included to facilitate opening of the closure system. The tightening mechanism in some embodiments includes a control for winding the lace into a housing to place tension on the lace thereby tightening the closure system.

30 Claims, 10 Drawing Sheets

Related U.S. Application Data

(60) Provisional application No. 60/843,830, filed on Sep. 12, 2006.

(51) Int. Cl.
 *A43C 11/14* (2006.01)
 *A43C 11/16* (2006.01)

(58) Field of Classification Search
 USPC .............. 602/5, 23, 27; 36/50.1, 50.5, 117.7
 See application file for complete search history.

(56) References Cited

U.S. PATENT DOCUMENTS

| | | | |
|---|---|---|---|
| 117,530 A | 8/1871 | Foote | |
| 228,946 A | 6/1880 | Schulz | |
| 230,759 A | 8/1880 | Drummond | |
| 379,113 A | 3/1888 | Hibberd | |
| 568,056 A | 9/1896 | Vail, Jr. | |
| 746,563 A | 12/1903 | McMahon | |
| 908,704 A | 1/1909 | Sprinkle | |
| 1,060,422 A | 4/1913 | Bowdish | |
| 1,062,511 A | 5/1913 | Short | |
| 1,090,438 A | 3/1914 | Worth et al. | |
| 1,170,472 A | 2/1916 | Barber | |
| 1,288,859 A | 12/1918 | Feller et al. | |
| 1,368,971 A | 2/1921 | Ross | |
| 1,393,188 A | 10/1921 | Whiteman | |
| 1,469,661 A | 2/1922 | Migita | |
| 1,412,486 A | 4/1922 | Paine | |
| 1,416,203 A | 5/1922 | Hobson | |
| 1,481,903 A | 4/1923 | Hart | |
| 1,466,673 A | 9/1923 | Solomon et al. | |
| 1,530,713 A | 2/1924 | Clark | |
| 1,995,243 A | 6/1934 | Clarke | |
| 2,088,851 A | 8/1937 | Gantenbein | |
| 2,109,751 A | 3/1938 | Matthias et al. | |
| 2,124,310 A | 9/1938 | Murr, Jr. | |
| 2,316,102 A | 4/1943 | Preston | |
| 2,539,026 A | 1/1951 | Mangold | |
| 2,611,940 A | 9/1952 | Cairns | |
| 2,673,381 A | 3/1954 | Dueker | |
| 2,907,086 A | 10/1959 | Ord | |
| 2,991,523 A | 7/1961 | Del Conte | |
| 3,028,602 A | 4/1962 | Miller | |
| 3,035,319 A | 5/1962 | Wolff | |
| 3,112,545 A | 12/1963 | Williams | |
| 3,163,900 A | 1/1965 | Martin | |
| 3,169,325 A | 2/1965 | Fesl | |
| 3,197,155 A | 7/1965 | Chow | |
| 3,221,384 A | 12/1965 | Aufenacker | |
| 3,276,090 A | 10/1966 | Nigon | |
| 3,401,437 A | 9/1968 | Christpohersen | |
| 3,430,303 A | 3/1969 | Perrin et al. | |
| 3,491,465 A | 1/1970 | Martin | |
| 3,545,106 A | 12/1970 | Martin | |
| 3,618,232 A | 11/1971 | Shnuriwsky | |
| 3,668,791 A | 6/1972 | Salzman et al. | |
| 3,678,539 A | 7/1972 | Graup | |
| 3,703,775 A | 11/1972 | Gatti | |
| 3,729,779 A | 5/1973 | Porth | |
| 3,738,027 A | 6/1973 | Schoch | |
| 3,793,749 A | 2/1974 | Gertsch et al. | |
| 3,808,644 A | 5/1974 | Schoch | |
| 3,834,048 A | 9/1974 | Maurer | |
| 3,934,346 A | 1/1976 | Sasaki et al. | |
| 3,975,838 A | 8/1976 | Martin | |
| 4,081,916 A * | 4/1978 | Salisbury | A43C 11/008 36/50.1 |
| 4,095,354 A | 6/1978 | Annovi | |
| 4,130,949 A | 12/1978 | Seidel | |
| 4,142,307 A | 3/1979 | Martin | |
| 4,227,322 A | 10/1980 | Annovi | |
| 4,261,081 A | 4/1981 | Lott | |
| 4,267,622 A | 5/1981 | Burnett-Johnston | |
| 4,408,403 A | 10/1983 | Martin | |
| 4,414,761 A * | 11/1983 | Mahood | A43C 1/00 24/712 |
| 4,433,456 A | 2/1984 | Baggio | |
| 4,433,679 A | 2/1984 | Mauldin et al. | |
| 4,463,761 A | 8/1984 | Pols et al. | |
| 4,480,395 A | 11/1984 | Schoch | |
| 4,551,932 A | 11/1985 | Schoch | |
| 4,555,830 A | 12/1985 | Petrini et al. | |
| 4,574,500 A | 3/1986 | Aldinio et al. | |
| 4,616,524 A | 10/1986 | Biodia | |
| 4,619,057 A | 10/1986 | Sartor et al. | |
| 4,620,378 A | 11/1986 | Sartor | |
| 4,631,839 A | 12/1986 | Bonetti et al. | |
| 4,631,840 A | 12/1986 | Gamm | |
| 4,633,599 A | 1/1987 | Morell et al. | |
| 4,654,985 A | 4/1987 | Chalmers | |
| 4,660,300 A | 4/1987 | Morell et al. | |
| 4,660,302 A | 4/1987 | Arieh et al. | |
| 4,680,878 A | 7/1987 | Pozzobon et al. | |
| 4,719,670 A | 1/1988 | Kurt | |
| 4,719,709 A | 1/1988 | Vaccari | |
| 4,719,710 A | 1/1988 | Pozzobon | |
| 4,722,477 A | 2/1988 | Floyd | |
| 4,741,115 A | 5/1988 | Pozzobon | |
| 4,748,726 A | 6/1988 | Schoch | |
| 4,760,653 A | 8/1988 | Baggio | |
| 4,780,969 A | 11/1988 | White, Jr. | |
| 4,787,124 A | 11/1988 | Pozzobon et al. | |
| 4,790,081 A | 12/1988 | Benoit et al. | |
| 4,796,829 A | 1/1989 | Pozzobon et al. | |
| 4,799,297 A | 1/1989 | Baggio et al. | |
| 4,802,291 A | 2/1989 | Sartor | |
| 4,811,503 A | 3/1989 | Iwama | |
| 4,826,098 A | 5/1989 | Pozzobon et al. | |
| 4,841,649 A | 6/1989 | Baggio et al. | |
| 4,856,207 A | 8/1989 | Datson | |
| 4,870,723 A | 10/1989 | Pozzobon et al. | |
| 4,870,761 A | 10/1989 | Tracy | |
| 4,884,760 A | 12/1989 | Baggio et al. | |
| 4,937,953 A | 7/1990 | Walkhoff | |
| 4,961,544 A | 10/1990 | Biodia | |
| 5,001,817 A | 3/1991 | De Bortoli et al. | |
| 5,016,327 A | 5/1991 | Klausner | |
| 5,027,482 A * | 7/1991 | Torppey | A43C 11/1493 24/306 |
| 5,042,177 A | 8/1991 | Schoch | |
| 5,062,225 A | 11/1991 | Gorza | |
| 5,065,480 A | 11/1991 | De Bortoli | |
| 5,065,481 A | 11/1991 | Walkhoff | |
| 5,108,216 A | 4/1992 | Geyer et al. | |
| 5,117,567 A | 6/1992 | Berger | |
| 5,129,130 A | 7/1992 | Lecouturier | |
| 5,152,038 A | 10/1992 | Schoch | |
| 5,157,813 A | 10/1992 | Carroll | |
| 5,158,428 A | 10/1992 | Gessner et al. | |
| 5,167,612 A | 12/1992 | Bonutti | |
| 5,177,882 A | 1/1993 | Berger | |
| 5,178,137 A | 1/1993 | Goor et al. | |
| 5,181,331 A | 1/1993 | Berger | |
| 5,184,378 A | 2/1993 | Batra | |
| D333,552 S | 3/1993 | Berger et al. | |
| 5,213,094 A | 5/1993 | Bonutti | |
| 5,249,377 A | 10/1993 | Walkhoff | |
| 5,259,094 A | 11/1993 | Zepeda | |
| 5,315,741 A | 5/1994 | Debberke | |
| 5,319,868 A | 6/1994 | Hallenbeck | |
| 5,325,613 A | 7/1994 | Sussmann | |
| 5,327,662 A | 7/1994 | Hallenbeck | |
| 5,335,401 A | 8/1994 | Hanson | |
| 5,341,583 A | 8/1994 | Hallenbeck | |
| 5,345,697 A | 9/1994 | Quellais | |
| 5,346,461 A | 9/1994 | Heinz et al. | |
| 5,353,483 A * | 10/1994 | Louviere | A43B 11/00 24/71 SK |
| 5,355,596 A | 10/1994 | Sussmann | |
| 5,357,654 A | 10/1994 | Hsing-Chi | |
| 5,357,691 A * | 10/1994 | Hyde | A43B 23/26 36/50.1 |

(56) References Cited

U.S. PATENT DOCUMENTS

| | | | |
|---|---|---|---|
| 5,365,947 A | 11/1994 | Bonutti | |
| 5,381,609 A | 1/1995 | Hieblinger | |
| 5,395,304 A | 3/1995 | Tarr et al. | |
| 5,425,161 A | 6/1995 | Schoch | |
| 5,425,185 A | 6/1995 | Gansler | |
| 5,430,960 A | 7/1995 | Richardson | |
| 5,433,648 A | 7/1995 | Frydman | |
| 5,437,617 A | 8/1995 | Heinz et al. | |
| 5,456,268 A | 10/1995 | Bonutti | |
| 5,463,822 A | 11/1995 | Miller | |
| 5,469,640 A * | 11/1995 | Nichols | A43C 1/00 24/306 |
| 5,469,940 A | 11/1995 | Nichols | |
| 5,477,593 A | 12/1995 | Leick | |
| 5,502,902 A | 4/1996 | Sussmann | |
| 5,511,325 A | 4/1996 | Hieblinger | |
| 5,526,585 A | 6/1996 | Brown et al. | |
| 5,535,531 A | 7/1996 | Karabed et al. | |
| 5,537,763 A | 7/1996 | Donnadieu et al. | |
| 5,557,864 A | 9/1996 | Marks | |
| 5,566,474 A | 10/1996 | Leick et al. | |
| 5,596,820 A | 1/1997 | Edauw et al. | |
| 5,599,000 A | 2/1997 | Bennett | |
| 5,599,288 A | 2/1997 | Shirley et al. | |
| 5,600,874 A | 2/1997 | Jungkind | |
| 5,606,778 A | 3/1997 | Jungkind | |
| 5,619,747 A | 4/1997 | Boisclair et al. | |
| 5,638,588 A | 6/1997 | Jungkind | |
| 5,640,785 A | 6/1997 | Egelja | |
| 5,647,104 A | 7/1997 | James | |
| 5,651,198 A | 7/1997 | Sussmann | |
| 5,669,116 A | 9/1997 | Jungkind | |
| 5,685,830 A | 11/1997 | Bonutti | |
| 5,718,021 A | 2/1998 | Tatum | |
| 5,718,065 A | 2/1998 | Locker | |
| 5,732,483 A | 3/1998 | Cagliari | |
| 5,736,696 A | 4/1998 | Del Rosso | |
| 5,737,854 A | 4/1998 | Sussmann | |
| 5,755,044 A | 5/1998 | Veylupek | |
| D394,745 S | 6/1998 | Egelja | |
| 5,761,777 A | 6/1998 | Leick | |
| 5,772,146 A | 6/1998 | Kawamoto et al. | |
| 5,784,809 A | 7/1998 | McDonald | |
| 5,819,378 A | 10/1998 | Doyle | |
| 5,833,640 A | 11/1998 | Vazquez, Jr. et al. | |
| 5,891,061 A | 4/1999 | Kaiser | |
| 5,901,912 A * | 5/1999 | Voorberg | B02C 21/00 241/117 |
| 5,934,599 A | 8/1999 | Hammerslag | |
| 5,956,823 A | 9/1999 | Borel | |
| 5,971,946 A * | 10/1999 | Quinn | A61F 5/0127 602/27 |
| 6,038,791 A | 3/2000 | Cornelius et al. | |
| 6,070,886 A | 6/2000 | Cornelius et al. | |
| 6,070,887 A | 6/2000 | Cornelius et al. | |
| 6,052,921 A | 8/2000 | Oreck | |
| 6,102,412 A | 8/2000 | Staffaroni | |
| 6,119,318 A | 9/2000 | Maurer | |
| 6,128,835 A | 10/2000 | Ritter et al. | |
| 6,128,836 A | 10/2000 | Thierry | |
| 6,148,489 A | 11/2000 | Dickie et al. | |
| 6,202,953 B1 | 3/2001 | Hammerslag | |
| 6,256,798 B1 | 7/2001 | Egolf et al. | |
| 6,267,390 B1 | 7/2001 | Maravetz et al. | |
| 6,289,558 B1 | 9/2001 | Hammerslag | |
| 6,416,074 B1 * | 7/2002 | Maravetz | A43B 5/0401 280/613 |
| 6,464,657 B1 | 10/2002 | Castillo | |
| 6,467,195 B2 | 10/2002 | Pierre et al. | |
| 6,477,793 B1 | 11/2002 | Pruitt et al. | |
| 6,543,159 B1 | 4/2003 | Carpenter | |
| 6,568,103 B2 | 5/2003 | Durocher | |
| 6,671,980 B1 * | 1/2004 | Liu | A43B 11/00 24/712 |
| 6,685,662 B1 | 2/2004 | Curry et al. | |
| 6,689,080 B2 | 2/2004 | Castillo | |
| 6,694,643 B1 | 2/2004 | Hsu | |
| 6,708,376 B1 | 3/2004 | Landry | |
| 6,711,787 B2 | 3/2004 | Jungkind et al. | |
| 6,757,991 B2 | 7/2004 | Sussmann | |
| 6,775,928 B2 | 8/2004 | Grande et al. | |
| 6,793,641 B2 | 9/2004 | Freeman et al. | |
| 6,796,951 B2 | 9/2004 | Freeman et al. | |
| 6,802,439 B2 | 10/2004 | Azam et al. | |
| 6,877,256 B2 | 4/2005 | Martin et al. | |
| 6,922,917 B2 | 8/2005 | Kerns et al. | |
| 6,938,913 B2 | 9/2005 | Elkington | |
| 6,942,632 B2 | 9/2005 | Cho | |
| 6,945,543 B2 | 9/2005 | De Bortoli et al. | |
| 6,962,571 B2 | 11/2005 | Castillo | |
| 6,976,972 B2 | 12/2005 | Bradshaw | |
| 6,993,859 B2 | 2/2006 | Martin et al. | |
| 7,076,843 B2 | 7/2006 | Sakabayashi | |
| 7,082,701 B2 | 8/2006 | Dalgaard et al. | |
| 7,134,224 B2 | 11/2006 | Elkington et al. | |
| 7,182,740 B1 | 2/2007 | Castillo | |
| 7,198,610 B2 | 4/2007 | Ingimundarson et al. | |
| 7,281,341 B2 | 10/2007 | Reagan et al. | |
| 7,293,373 B2 | 11/2007 | Reagan et al. | |
| 7,314,458 B2 | 1/2008 | Bodenschatz | |
| 7,331,126 B2 | 2/2008 | Johnson | |
| 7,367,522 B2 | 5/2008 | Chen | |
| 7,386,947 B2 | 6/2008 | Martin et al. | |
| 7,402,147 B1 | 7/2008 | Allen | |
| 7,442,177 B1 | 10/2008 | Garelick et al. | |
| 7,490,458 B2 | 2/2009 | Ford | |
| 7,516,914 B2 | 4/2009 | Kovacevich et al. | |
| 7,584,528 B2 | 9/2009 | Hu | |
| 7,591,050 B2 | 9/2009 | Hammerslag | |
| 7,597,675 B2 | 10/2009 | Ingimundarson et al. | |
| 7,600,660 B2 | 10/2009 | Kasper et al. | |
| 7,617,573 B2 | 11/2009 | Chen | |
| 7,618,386 B2 | 11/2009 | Nordt, III et al. | |
| 7,618,389 B2 | 11/2009 | Nordt, III et al. | |
| 7,648,404 B1 | 1/2010 | Martin | |
| 7,662,122 B2 | 2/2010 | Sterling | |
| 7,694,354 B2 | 4/2010 | Philpott et al. | |
| 7,704,219 B2 | 4/2010 | Nordt, III et al. | |
| 7,713,225 B2 | 5/2010 | Ingimundarson et al. | |
| 7,789,844 B1 | 9/2010 | Allen | |
| 7,794,418 B2 | 9/2010 | Ingimundarson et al. | |
| 7,806,842 B2 | 10/2010 | Stevenson et al. | |
| 7,819,830 B2 | 10/2010 | Sindel et al. | |
| 7,871,334 B2 | 1/2011 | Young et al. | |
| 7,877,845 B2 | 2/2011 | Signori | |
| 7,878,998 B2 | 2/2011 | Nordt, III et al. | |
| 7,887,500 B2 | 2/2011 | Nordt, III et al. | |
| 7,896,827 B2 | 3/2011 | Ingimundarson et al. | |
| 7,908,769 B2 | 3/2011 | Pellegrini | |
| 7,922,680 B2 | 4/2011 | Nordt et al. | |
| 7,935,068 B2 | 5/2011 | Einarsson | |
| 7,947,005 B2 | 5/2011 | Castillo | |
| 7,950,112 B2 | 5/2011 | Hammerslag | |
| 7,954,204 B2 | 6/2011 | Hammerslag | |
| 7,963,049 B2 | 6/2011 | Messmer | |
| 7,992,261 B2 | 8/2011 | Hammerslag | |
| 7,993,296 B2 | 8/2011 | Nordt, III et al. | |
| 8,016,781 B2 | 9/2011 | Ingimundarson et al. | |
| 8,056,150 B2 | 11/2011 | Stokes et al. | |
| 8,091,182 B2 | 1/2012 | Hammerslag | |
| 8,105,252 B2 | 1/2012 | Rousso | |
| 8,109,015 B2 | 2/2012 | Signori | |
| 8,128,587 B2 | 3/2012 | Stevenson et al. | |
| 8,231,074 B2 | 7/2012 | Hu et al. | |
| 8,231,560 B2 | 7/2012 | Ingimundarson et al. | |
| 8,245,371 B2 | 8/2012 | Chen | |
| 8,277,401 B2 | 10/2012 | Hammerslag et al. | |
| 8,277,404 B2 | 10/2012 | Einarsson | |
| 8,303,527 B2 | 11/2012 | Joseph | |
| 8,308,098 B2 | 11/2012 | Chen | |
| 8,679,042 B2 | 3/2014 | Kausek | |
| 2002/0052568 A1 | 5/2002 | Houser et al. | |

(56) References Cited

U.S. PATENT DOCUMENTS

| | | | |
|---|---|---|---|
| 2002/0095750 A1* | 7/2002 | Hammerslag | A43B 5/16 24/68 SK |
| 2002/0178548 A1 | 12/2002 | Freed | |
| 2003/0171706 A1 | 9/2003 | Nelson | |
| 2003/0177662 A1 | 9/2003 | Elkington et al. | |
| 2005/0081403 A1 | 4/2005 | Mathieu | |
| 2005/0087115 A1 | 4/2005 | Martin | |
| 2005/0098673 A1 | 5/2005 | Huang | |
| 2005/0102861 A1 | 5/2005 | Martin | |
| 2005/0198866 A1 | 9/2005 | Wiper | |
| 2005/0273025 A1 | 12/2005 | Houser | |
| 2006/0053658 A1 | 3/2006 | Voughlohn | |
| 2006/0156517 A1 | 7/2006 | Hammerslag et al. | |
| 2006/0179685 A1 | 8/2006 | Borel et al. | |
| 2007/0113524 A1 | 5/2007 | Lander | |
| 2007/0128959 A1 | 6/2007 | Cooke | |
| 2007/0169378 A1 | 7/2007 | Sodeberg et al. | |
| 2007/0276306 A1 | 11/2007 | Castillo | |
| 2008/0060167 A1 | 3/2008 | Hammerslag | |
| 2009/0019734 A1* | 1/2009 | Reagan | A43B 3/0031 36/115 |
| 2009/0099562 A1 | 4/2009 | Ingimundarson et al. | |
| 2009/0124948 A1 | 5/2009 | Ingimundarson et al. | |
| 2009/0172928 A1 | 7/2009 | Messmer et al. | |
| 2009/0172929 A1 | 7/2009 | Hwang | |
| 2009/0184189 A1 | 7/2009 | Soderberg | |
| 2009/0287128 A1 | 11/2009 | Ingimundarson et al. | |
| 2010/0081979 A1 | 4/2010 | Ingimundarson et al. | |
| 2010/0094189 A1 | 4/2010 | Ingimundarson et al. | |
| 2010/0101061 A1 | 4/2010 | Ha | |
| 2010/0139057 A1 | 6/2010 | Soderberg | |
| 2010/0174221 A1 | 7/2010 | Ingimundarson et al. | |
| 2010/0217169 A1 | 8/2010 | Ingimundarson | |
| 2010/0299959 A1 | 12/2010 | Hammerslag | |
| 2010/0331750 A1 | 12/2010 | Ingimundarson | |
| 2011/0000173 A1 | 1/2011 | Lander | |
| 2011/0098618 A1 | 4/2011 | Fleming | |
| 2011/0144554 A1 | 6/2011 | Weaver, II et al. | |
| 2011/0167543 A1 | 7/2011 | Kovacevich et al. | |
| 2011/0178448 A1 | 7/2011 | Einarsson | |
| 2011/0184326 A1 | 7/2011 | Ingimundarson et al. | |
| 2011/0218471 A1 | 9/2011 | Ingimundarson et al. | |
| 2011/0225843 A1 | 9/2011 | Kerns et al. | |
| 2011/0266384 A1 | 11/2011 | Goodman et al. | |
| 2011/0288461 A1 | 11/2011 | Arnould et al. | |
| 2011/0301521 A1 | 12/2011 | Weissenbock et al. | |
| 2011/0306911 A1 | 12/2011 | Tran | |
| 2012/0000091 A1 | 1/2012 | Cotterman et al. | |
| 2012/0004587 A1 | 1/2012 | Nickel et al. | |
| 2012/0010547 A1 | 1/2012 | Hinds | |
| 2012/0029404 A1 | 2/2012 | Weaver, II et al. | |
| 2012/0246974 A1 | 10/2012 | Hammerslag et al. | |
| 2013/0025100 A1 | 1/2013 | Ha | |
| 2013/0269219 A1 | 10/2013 | Burns et al. | |
| 2013/0277485 A1 | 10/2013 | Soderberg et al. | |
| 2014/0117140 A1 | 5/2014 | Goodman et al. | |
| 2015/0026936 A1 | 1/2015 | Kerns et al. | |
| 2015/0033519 A1 | 2/2015 | Hammerslag et al. | |

FOREIGN PATENT DOCUMENTS

| | | |
|---|---|---|
| CA | 2112789 | 8/1994 |
| CA | 2114387 | 8/1994 |
| CH | 41765 | 9/1907 |
| CH | 111341 | 11/1925 |
| CH | 199766 | 11/1938 |
| CH | 204 834 A | 8/1939 |
| CN | 2613167 Y | 4/2004 |
| CN | 201015448 Y | 2/2008 |
| DE | 555211 | 7/1932 |
| DE | 641976 | 2/1937 |
| DE | 1 661 668 | 8/1953 |
| DE | 7043154 | 3/1971 |
| DE | 7045778 | 3/1971 |
| DE | 1 785 220 | 5/1971 |
| DE | 2 062 795 | 6/1972 |
| DE | 7047038 | 1/1974 |
| DE | 23 41 658 | 3/1974 |
| DE | 24 14 439 | 10/1975 |
| DE | 29 00 077 A1 | 7/1980 |
| DE | 29 14 280 A1 | 10/1980 |
| DE | 31 01 952 A1 | 9/1982 |
| DE | 81 01 488 | 7/1984 |
| DE | 38 13 470 A1 | 11/1989 |
| DE | 3822113 C2 | 1/1990 |
| DE | 43 02 401 A1 | 8/1994 |
| DE | 94 13 147 U | 10/1994 |
| DE | 93 15 776 | 2/1995 |
| DE | 295 03 552 | 4/1995 |
| DE | 196 24 553 A1 | 1/1998 |
| DE | 19945045 A1 | 9/1999 |
| DE | 201 16 755 U1 | 1/2002 |
| EP | 0 589 232 A1 | 3/1994 |
| EP | 0 589 233 A1 | 3/1994 |
| EP | 0 614 624 | 9/1994 |
| EP | 0 614 625 A1 | 9/1994 |
| EP | 0 651 954 A1 | 5/1995 |
| EP | 0 693 260 | 1/1996 |
| EP | 0 734 662 A1 | 10/1996 |
| EP | 1 236 412 A | 9/2002 |
| FR | 1 349 832 | 1/1964 |
| FR | 1 374 110 | 10/1964 |
| FR | 1 404 799 | 7/1965 |
| FR | 2 019 991 A | 7/1970 |
| FR | 2 108 428 | 5/1972 |
| FR | 2 173 451 | 10/1973 |
| FR | 2 175 684 | 10/1973 |
| FR | 2 399 811 | 3/1979 |
| FR | 2 565 795 A1 | 12/1985 |
| FR | 2 598 292 A1 | 11/1987 |
| FR | 2 770 379 A1 | 5/1999 |
| FR | 2 814 919 A1 | 4/2002 |
| GB | 11673 | 6/1899 |
| GB | 216400 | 5/1924 |
| IT | 1220811 | 3/1998 |
| IT | PD 2003 A 000197 | 3/2005 |
| IT | PD 2003 A 000198 | 3/2005 |
| JP | 8-9202 | 6/1933 |
| JP | 49-28618 | 3/1974 |
| JP | 51-2776 | 1/1976 |
| JP | 51-121375 | 10/1976 |
| JP | 51-131978 | 10/1976 |
| JP | 53-124987 | 3/1977 |
| JP | 54-108125 | 1/1978 |
| JP | 62-57346 | 4/1987 |
| JP | S63-3857 | 1/1988 |
| JP | 63-80736 | 5/1988 |
| JP | H02-236025 | 9/1990 |
| JP | 3030988 | 3/1991 |
| JP | 3031760 | 3/1991 |
| JP | 5-228169 | 9/1993 |
| JP | 7-208 | 1/1995 |
| JP | H07-018613 | 6/1995 |
| JP | 8-131201 | 5/1996 |
| JP | 10-199366 | 7/1998 |
| JP | 2004-016732 | 1/2004 |
| JP | 2004-041666 | 2/2004 |
| JP | 2005-124597 | 5/2005 |
| KR | 20-0367882 | 11/2004 |
| KR | 20-0400568 | 11/2005 |
| KR | 10-0598627 | 7/2006 |
| WO | WO 81/01645 | 6/1981 |
| WO | WO 94/27456 | 12/1994 |
| WO | WO 1995/03720 | 2/1995 |
| WO | WO 1998/37782 | 9/1998 |
| WO | WO 1999/15043 A1 | 4/1999 |
| WO | WO 2000/53045 | 9/2000 |
| WO | WO 2000/76337 A1 | 12/2000 |

(56) References Cited

FOREIGN PATENT DOCUMENTS

WO     WO 2001/08525 A1     2/2001
WO     WO 2007/016983 A1     2/2007

OTHER PUBLICATIONS

U.S. Appl. No. 13/273,060 including its prosecution history, filed Oct. 13, 2011, Soderberg, et al.
U.S. Appl. No. 13/793,919 including its prosecution history, filed Mar. 11, 2013, Cotterman, et al.
ASOLO® Boot Brochure Catalog upon information and belief date is as early as Aug. 22, 1997.
International Search Report and the Written Opinion in PCT/US2007/078327 dated Apr. 28, 2008 in 18 pages.
International Preliminary Report on Patentability in PCT/US2007/078327 dated Mar. 26, 2009 in 11 pages.
U.S. Appl. No. 13/865,951 Including its prosecution history, filed Apr. 18, 2013, Soderberg, et al.

\* cited by examiner

CLOSURE SYSTEM FOR BRACES, PROTECTIVE WEAR AND SIMILAR ARTICLES

This application is a continuation of U.S. patent application Ser. No. 11/854,522, filed Sep. 12, 2007, which claims the benefit of U.S. Provisional Patent Application No. 60/843,830, filed Sep. 12, 2006, the entireties of which are hereby incorporated by reference and made a part of this specification for all that they disclose.

This application hereby incorporates by reference in their entireties U.S. patent application Ser. No. 11/263,253, filed Oct. 31, 2005, published Jul. 20, 2006 under publication number 2006-0156517 A1, now abandoned, and U.S. patent application Ser. No. 11/650,665, filed Jan. 8, 2007, published Jul. 25, 2007 under publication number 2007-0169378 A1, now abandoned.

These inventions relate to braces, protective wear and similar articles worn on the body or appendages of humans and animals. More particularly, these inventions relate generally to low-friction closure systems that provide equilibrated tightening pressure for a brace, protective wear or other similar article.

BACKGROUND OF THE INVENTION

Orthopedic supports are typically used to stabilize and protect various limbs of the human anatomy from sustaining or worsening an injury. Typically, orthopedic braces have been used on elbows, wrists, knees and ankles. The purpose of an orthopedic brace is to reduce strain on the injured limb while permitting the limb to continue its function, minimizing the risk of either a more damaging injury or renewing an old injury.

One significant problem with orthopedic braces used during athletic activities is the tendency of the orthopedic braces to shift as adjacent muscles tense and relax. For example, knee braces often ride down an athlete's leg when the athlete runs. When this problem is approached by tightening a conventional strapping mechanism, discomfort and restriction of circulation occurs. Even partial shifting of a typical orthopedic brace interferes with its proper operation, and so an athlete must choose between a properly oriented brace and a comfortable one.

Another problem with conventional braces is the bulky fittings used to couple straps. D-ring strap fittings usually depend from fittings that are attached to the brace by rivets or other fastening structures. Whenever the cuff structures have such extraneous additional structure for fitting the straps, user discomfort is increased from the added bulk and complexity, and a low profile is difficult to achieve.

Yet another problem with conventional braces is the lack of even compression of the soft tissues of the leg against the internal structure of the bones whose position and movement are to be controlled. As force is applied to a conventional brace, the brace tightens selectively near the tightened strap. This is particularly the case with a conventional brace that uses full circumference straps around, for example, a user's leg. As a load is applied to a conventional brace, the brace is free to distort, except where the straps are secure around the leg, and this distortion can allow the bones to misalign sufficiently to damage the ligaments about the knee. The typical strapping mechanism often does not adequately distribute the tightening force along the length of a tightening zone. Therefore, there are areas of higher and lower tension throughout the brace.

Another drawback associated with conventional strapping mechanisms is that it is often difficult to untighten or redistribute tension, as the wearer must loosen and readjust the straps and brace positioning.

Similar problems are present when protective wear or other articles or equipment are strapped to various parts of the body of a human or other animal. Such articles include, for example, shin guards for, for example, softball, baseball, soccer, or hockey, thigh guards, arm guards, shoulder guards or pads, etc.

There is, therefore, a need for a closure or tightening system for braces, protective wear and other similar articles that does not suffer from the aforementioned drawbacks. Such a system may facilitate automatic distribution of circumferential tightening forces along the braced or protected limbs or other body parts. The tightness of the article may desirably be easy to loosen and incrementally adjust. The tightening system may further close tightly and resist loosening with continued use.

SUMMARY OF THE INVENTION

In some embodiments, a brace closure system is disclosed. The closure system comprises a brace and a plurality of opposing lace guide members attached to the brace. The lacing system further comprises a lace extending through the guide members and coupled to a tightening mechanism which in turn may be coupled to the brace. The tightening mechanism includes a control for drawing the lace into and/or through the housing of the tightening mechanism to place tension on the lace thereby tightening the brace. In some embodiments, quick release members are provided to facilitate opening and closing of the brace. In some embodiments, one or more of the lace guides are slidingly attached to the brace. In some embodiments, the lace extends through a lacing zone and forms a crossing pattern as it crosses over itself. In some embodiments, the lace does not cross in the lacing zone. In some embodiments, one or more of the lace guides are indirectly coupled to the brace by the lace. In some embodiments, the guides are configured to release the lace to facilitate opening and closing of the brace.

In some embodiments, a closure system for use with an article of protective wear is disclosed. The closure system includes a plurality of lace guides, a tightening mechanism, a plurality of retaining members and one or more quick release members. The tightening mechanism is configured to draw the lace guides together to apply tension to the closing system. The quick release members are configured to facilitate opening and closing of the system. In some embodiments, one or more of the lace guides are slidingly attached to the article. In some embodiments, the lace extends through a lacing zone and forms a crossing pattern as it crosses over itself. In some embodiments, the lace does not cross in the lacing zone. In some embodiments, one or more of the lace guides are indirectly coupled to the article by the lace. In some embodiments, the guides are configured to release the lace to facilitate opening and closing of the article.

In some embodiments, a method of providing a closure system for an article is provided, the method including the steps of providing an article having at least one set of opposed guide members; a lace extending back and forth between the opposed guide members, the guide members and lace having a relatively low friction interface therebetween; a rotatable tightening mechanism on the article for retracting the lace, thereby advancing the opposed guide members towards each other to tighten the article; and a quick release member for releasing at least a portion of the closure system to allow complete opening of the article; coupling the release member, thereby closing the article; rotating the control to retract lace, thereby advancing the opposed guide members towards each other to tighten the article; and permitting the lace to slide through the guide members, to equilibrate tension along the length of the lacing system.

In some embodiments, a closure system for an article of protective wear is provided including at least one set of opposed guide members and a lace extending back and forth between the opposed guide members, the guide members and lace having a relatively low friction interface therebetween. A rotatable tightening mechanism is also provided and configured to apply tension on the lace, thereby advancing the opposed guide members towards each other. The system also includes a retaining member coupled by a quick release member to one of the opposed guide members, the retaining member configured to extend across an opening in the protective wear and the release member configured to facilitate opening and closing of the system, wherein the tightening mechanism permits final adjustment of the tension in the system.

In some embodiments, a brace closure system includes a brace with a plurality of opposing lace guide members attached thereto. A lace extends through the guide members and a rotatable tightening mechanism is attached to the brace and coupled to the lace, the tightening mechanism including a housing and a control for retracting the lace into the housing to place tension on the lace thereby tightening the brace.

In some embodiments, a method of closing an article comprising a closure system comprising a pair of opposing lace guides, a rotatable tightening mechanism comprising a housing and a control, a lace coupling the pair of lace guides and the tightening mechanism, a retaining member, and a release mechanism having a first component selectively couplable to a second component, wherein the first component is coupled to a lace guide and the second component is coupled to a retaining member includes the steps of coupling the first and second components of the release mechanism to couple the retaining member to the guide and rotating the control to draw the lace into the housing, thereby increasing the tension on the lace and drawing the opposing lace guides toward each other, wherein the guide members and the lace have a relatively low friction interface therebetween and the lace is permitted to slide through the guide members to equilibrate the tension in the system.

In some embodiments, a closure system for use with a brace, a protective article or other similar article having first and second opposing sides extending substantially parallel to each other to define a longitudinal axis of the article, the article configured to be worn on the body or limbs includes a plurality of lace guide pairs, with opposing guides positioned on the opposing sides, wherein the guides on the first side of the article are slidingly attached to the article. A lace extends back and forth between the opposed guides and a rotatable tightening mechanism is configured to apply tension on the lace, thereby advancing the opposed guides towards each other. Each of the guides defines a length extending substantially parallel to the longitudinal axis of the article and the guides one the first side of the article move in a substantially perpendicular direction to the longitudinal axis.

In some embodiments, a closure system for use with a brace, a protective article or other similar article having first and second opposing sides and configured to be worn on the body or limbs includes a plurality of lace guide pairs, with opposing guides positioned on the opposing sides. A lace extends back and forth between the opposed guides and a rotatable tightening mechanism is configured to apply tension on the lace, thereby advancing the opposed guides towards each other. A quick release mechanism is also included with first and second components, the quick release mechanism is configured to operate in substantially the same direction as the movement of the guides, wherein engagement of the first and second components supplies a tightening force in the direction of the guide movement.

In some embodiments, a closure system for use with a brace, a protective article or other similar article having first and second opposing sides and configured to be worn on the body or limbs includes a plurality of lace guide pairs, with opposing guides positioned on the opposing sides and a lace extending back and forth between the opposed guides. A rotatable tightening mechanism is configured to apply tension on the lace, thereby advancing the opposed guides towards each other and a plurality of retaining members having first and second ends is included wherein they extend between the first and second opposing sides. A plurality of quick release mechanisms with first and second components are also included, wherein the first components of the quick release mechanisms are attached to the guides on the first side of the article, the first ends of the retaining members are attached to the first components of the quick release mechanisms, and the second ends of the retaining members are attached to the second side of the article.

In some embodiments, a brace for use with an ankle/foot having first and second opposing sides comprises a plurality of lace guide pairs, with opposing guides positioned on the opposing sides, a lace extending back and forth between the opposed guides, a rotatable tightening mechanism configured to apply tension on the lace, thereby advancing the opposed guides towards each other, and a tongue configured to be positioned between the first and second sides when the brace is closed, wherein all of the guides on the first side of the brace permit release of the lace from the first side of the brace.

In some embodiments, a method is provided of closing an article including first and second opposing sides, a plurality of lace guide pairs with opposing guides positioned on the opposing sides; a lace extending back and forth between the opposed guides; a rotatable tightening mechanism configured to apply tension on the lace; a plurality of retaining members having first and second ends and extending between the first and second opposing sides; and a plurality of quick release mechanisms with first and second components, wherein the first components of the quick release mechanisms are attached to the guides on the first side of the article, the first ends of the retaining members are attached to the first components of the quick release mechanisms, and the second ends of the retaining members are attached to the second side of the article, the method including the steps of attaching first and second components of the quick release mechanisms to couple the retaining members to the guides on the first side of the article and rotating the tightening mechanism such that tension is applied to the lace, thereby advancing the opposed guides towards each other to close the article.

BRIEF DESCRIPTION OF THE DRAWINGS

These and other features, aspects, and advantages of the present inventions are described below with reference to drawings of several embodiments, which are intended to illustrate, but not to limit, the present inventions.

DETAILED DESCRIPTION OF PREFERRED EMBODIMENTS

Figure 1:
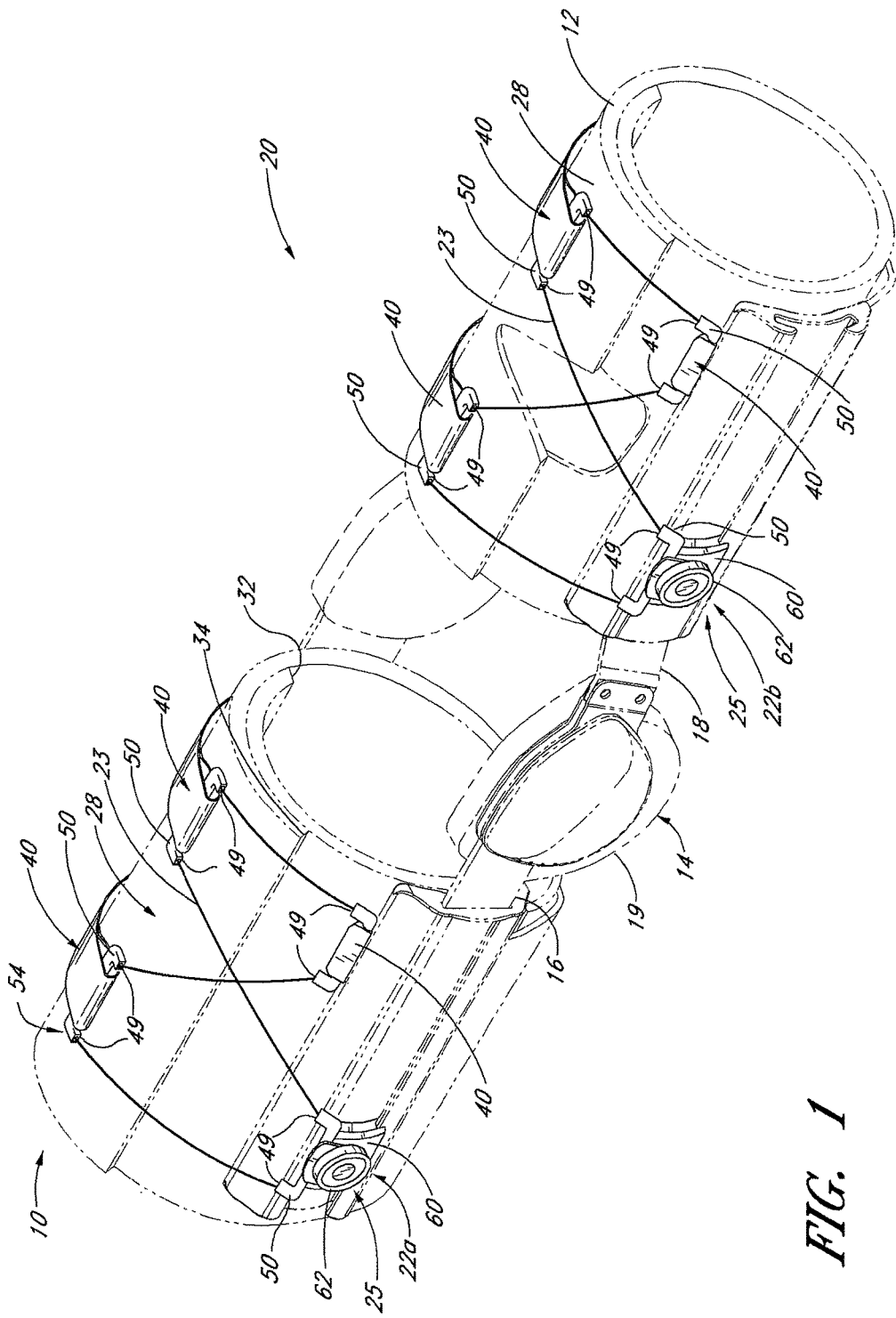
FIG. 1 is a perspective view of an orthopedic brace including a lacing system configured in accordance with one embodiment.

Referring to FIG. 1, one embodiment of an orthopedic brace 20 prepared in accordance with the present inventions is disclosed. The orthopedic brace 20 generally comprises a knee brace that is tightened around a wearer's leg using a lacing configuration comprising two lacing systems 22a, 22b, such that the knee brace substantially surrounds and protects the wearer's knee. The orthopedic brace of the illustrated embodiment is particularly concerned with relieving and/or supporting the knee joint.

Generally speaking, some knee braces function to counteract anterior shifting of the tibia when the anterior cruciate ligament is missing or damaged. Such anterior shifting of the tibia may occur for a variety of reasons and often happens when a person engages in physical activities that involve sudden turning to the right or to the left, sudden stopping, sudden jumping, running backwards or other types of movements. Where the anterior cruciate ligament is missing or damaged, such anterior shifting of the tibia can also occur when a person simply extends his or her leg from a flexed position towards its fully straightened position. Although this illustrated embodiment shows the lacing systems applied to knee braces, it is to be understood that the principles discussed herein are readily applicable to any of a variety of orthopedic braces, including ankle braces, wrist braces, foot braces, elbow braces and many other types of orthopedic braces well known to those of skill in the art. As would be well understood by those skilled in the art, slight changes may be made to make the exemplary brace suitable for such tasks. Similarly, it is to be understood that the principles discussed herein are readily applicable to any of a variety of articles or equipment designed to be worn on the body of a person or an animal, including shin guards for, for example, softball, baseball, soccer, or hockey, thigh guards, arm guards, shoulder guards or pads, etc. Examples of similar articles for animals include shin guards for horses.

In some embodiments, the lacing configuration of closure system comprises two distinct lacing systems 22a, 22b. In some embodiments, the lacing systems 22a, 22b function similarly. Of course, as would be well understood by those skilled in the art, the lacing systems 22a, 22b may differ in alternative embodiments in a number of ways, and may each comprise different embodiments disclosed herein. In some embodiments, each lacing system 22 includes a lace or cable 23 that is threaded through portions of the orthopedic brace and attached at opposite ends to a tightening mechanism 25, as described in further detail below. As used herein, the terms, lace and cable, have the same meaning unless specified otherwise. The lace 23 is preferably a low friction lace that slides relatively easily through the orthopedic brace 20 to facilitate automatic equilibration of the tightening of the orthopedic brace 20 over the length of the lacing zone.

The orthopedic brace 20 shown in FIG. 1 is constructed to fit a wearer's leg. The upper cuff 10 is formed to fit the wearer's thigh and curves around the thigh, generally conforming to the wearer's musculature. The lower cuff 12 is similar in construction to the upper cuff 10, and is formed to fit and curve around the wearer's calf. In some embodiments, the upper and lower cuffs 10, 12 are formed from a relatively lightweight, breathable material. In some embodiments, the cuffs 10, 12 are manufactured from a cloth, fabric, or foam-like material, as would be well-known to those skilled in the art.

The upper and lower cuffs 10, 12 are joined by at least one strut assembly 14, which may include an upper strut 16 and a lower strut 18 joined by a hinge assembly 19. The hinge assembly 19 preferably permits pivoting of the upper strut 16 relative to the lower strut 18, and associated bending of the wearer's knee. The upper strut 16 can be secured to the upper cuff 10 by any of a number of fastening devices, such as screws, adhesive, thread, or any other means of coupling these structures. The lower strut 18 may be similarly attached to the lower cuff 12.

As shown, each of the cuffs 10, 12 are generally formed from a single piece of material that is wrapped around itself, forming two ends 32, 34 that are drawn towards each other and, in fact, overlap. In some embodiments, the cuffs 10, 12 are connected by additional material in the region of the hinge assembly, often with an opening left for the front and/or the back of the wearer's knee. Generally, the lace 23 may be tensioned to draw the ends 32, 34 past each other and thereby tighten the orthopedic brace 20 about the wearer's limbs, as described in detail below. Although the ends 32, 34 are shown in an overlapping position, it should be understood that these ends might also be sized to be separated by some distance when the orthopedic brace 20 is tightened. Thus, references herein to opposing ends of an orthopedic brace refer merely to those portions attached to opposite sides of the lacing systems 22a, 22b. This reference is generic to braces or other articles that may or may not overlap. In both, tightening is accomplished by drawing opposing sides of the brace or article towards one another and more generally by drawing opposing sides of the lacing system toward each other.

Preferably, the outer surfaces 28 of the orthopedic brace cuffs 10, 12 are relatively low friction in order to facilitate sliding of the ends 32, 34 and the laces 23 over the surfaces 28 when the laces 23 are tightened. The low friction surfaces 28 may be formed integrally with the brace 20 or may be applied thereto by adhesives, heat bonding, stitching or the like. In one embodiment, an outer surface 28 of the brace 20 contacted by the lace 23 is formed by adhering a flexible layer of nylon or polytetrafluoroethylene to the outer surface.

As shown in FIG. 1, in some embodiments for each lacing system 22, the lace 23 is threaded in a crossing pattern along a generally forward-facing portion of the brace 20, between two generally parallel rows of side retaining members 40. The side retaining members 40 may consist of a strip of material attached to the brace 20 so as to define a space in which guides 50 are positioned. The lace 23 slides through the guides 50 during tightening and untightening of the lace 23, as described more fully below. In the illustrated embodiment, there is one side retaining member 40 on one side of an orthopedic lacing system 22, and two side retaining members 40 on the other. Of course, in other embodiments, the number of retaining members 40 may vary. In some embodiments, four, five or six retaining members 40 may be desirable. In some embodiments, the retaining members may have variable lengths, in order to better fit a wider variety of patients' legs. One such an embodiment is described in greater detail below with respect to FIGS. 2 through 4.

The guides 50 may be attached to the orthopedic brace 20 in any of a variety of ways, as will be appreciated by those of skill in the art. For example, the retaining members 40 can be deleted, and the guides 50 sewn directly into the orthopedic brace 20. Stitching the guides 50 directly to the orthopedic brace 20 may advantageously permit optimal control over the force distribution along the length of the guides 50. For example, when the lace 23 is under relatively high levels of tension, a guide 50 may start to bend and to possibly even kink. Bending of the guide members 50 under tension would increase friction between the guides 50 and the lace 23, and severe bending or kinking of the guide members 50 would undesirably interfere with the intended operation of the lacing systems 22. Therefore, the attachment mechanism for attaching the guide member 50 to the orthopedic brace 20 preferably provides sufficient support for the guide member to resist bending and/or kinking. Alternatively, or in addition to, the guide members themselves are constructed to resist bending and/or kinking. Sufficient support is particularly desirable on the inside radius of any curved portions, particularly near the ends of the guide members 50. In addition to the attachment mechanism providing resistance to bending, the guide members 50 themselves may be formed so as to resist bending.

In some embodiments, each of the guide members 50 defines a pair of openings 49 that communicate with opposite ends of a lumen 54 extending therethrough. The openings 49 function as inlets/outlets for the lace 23. The openings 49 are desirably at least as wide as the cross-section of the lumen 54.

As the lacing system 22 is tightened, the spacing distance between opposing guide members 50 will also be reduced. For some products, the wearer may prefer to tighten certain portions of the brace more than others. Said in another way, the wearer may prefer zonal tightening on the brace, wherein different zones may have different tightness. In some embodiments, this can be conveniently accomplished by limiting the ability of the certain opposing guides 50 to move towards each other beyond a preselected minimum distance during the tightening process. For this purpose, a selection of spacers, dynamic spacers or stops (not shown) having an assortment of lengths may be provided with a lacing system 22. In general, these limiters create zonal tightening on the brace to enhance the customization of tightening pressure according to the wearer's wants or needs. Additional ways of creating zonal tightening are also possible. For example, additional tightening mechanisms 25 may be used. In some embodiments, a tightening mechanism 25 is provided for each pair of opposing lace guides. In the embodiment illustrated in FIG. 1, three or four tightening mechanisms 25 could be provided to allow additional customization of the tightening pressure on the brace 20. In some embodiments, specialized lace guides may be used to create zonal tightening. In one embodiment, a slot and a guide are provided in generally the same location on the brace such that the lace can be doubled up in that location to increase the tightness in that location. In some embodiments, combining multiple tightening mechanisms and specialized lacing arrangements can also provide zonal tightening. Examples of zonal tightening are described in greater detail in U.S. Patent Publication No. 2006-0156517, incorporated herein by reference in its entirety.

In the illustrated embodiment, the guide members 50 each have a general "U" shape that opens towards the mid-lines of the lacing systems 22. Preferably, each of the guide members 50 comprises a longitudinal dimension measured between the openings 49. The length of the longitudinal dimension may be varied to adjust the distribution of the closing pressure that the lace 23 applies to the orthopedic brace 20 when the lace 23 is under tension. In addition, the length of the longitudinal dimension need not be the same for all guide members 50 on a particular brace. For example, the longitudinal dimensions may be shortened along portions of the brace 20 further from the hinge assembly 19, in order to increase the closing pressures that the lace 23 applies to those portions of the leg. In general, the length of the longitudinal dimension will fall within the range of about ½ inch to about 3 inches, and, in some embodiments, within the range of about ¼ inch to about 4 inches. The shorter the longitudinal dimension between the openings 49, the greater the closing pressure tends to be in that particular portion of the lacing zone.

The guide members 50 are preferably manufactured from a low friction material, such as a lubricious polymer or metal, that facilitates the sliding of the lace 23 therethrough. Alternatively, the guides 50 can be made from any convenient, substantially rigid material, and can then be coated with a lubricious coating on at least the sliding in order to decrease friction. The guide members 50 are preferably substantially rigid to prevent bending and kinking of the guide members 50 and/or the lace 23 within any of the guide members 50, as the lace 23 is tightened.

Figure 8A:
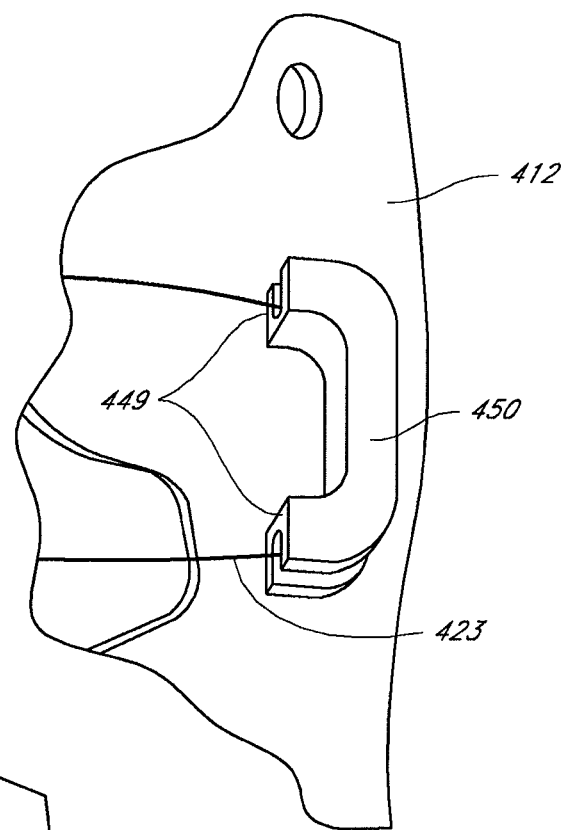
FIG. 8A is an exploded view of a portion designated 8A-8A in FIG. 7.

Alternatively, the guide members may comprise an open channel having, for example, a semicircular or "U" shaped cross-section (see, for example, FIG. 8A shown in conjunction with another embodiment). The guide channel is preferably mounted such that the channel opening faces away from the midline of the lacing systems, so that a lace under tension will be retained therein. In some embodiments, one or more retention strips, stitches or flaps may be provided for "closing" the open side of the channel, to prevent the lace from escaping when tension on the lace is released. In other embodiments, the open side of the channel is left open to facilitate removal of the lace from the guide to allow the opening of the article to increase beyond what would otherwise be permitted if the lace was fixed in the channel. A larger opening may be advantageous, when, for example, it is difficult to fit an appendage into the article due to injury.

Alternatively, in some embodiments the guide members are closed, but are configured to be removably attached to the brace such that a larger opening may be created by removing the guide and lace from the brace. In some embodiments, various combinations of these guide members may be employed.

Several guide channels may be molded as a single piece, and may be molded to a common backing support strip that can then be adhered or stitched to the brace. Such a configuration is illustrated in, for example, FIGS. 5 and 6. Examples of guide members are described in greater detail in U.S. Patent Publication Nos. 2006-0156517 and 2007-0169378, incorporated herein by reference in their entireties.

The lace 23 may be formed from any of a wide variety of polymeric or metal materials or combinations thereof that exhibit sufficient axial strength and bendability for the present application. For example, any of a wide variety of solid core wires, solid core polymers, or multi-filament wires or polymers, which may be woven, braided, twisted or otherwise configured, can be used. A solid or multi-filament metal core can be provided with a polymeric coating, such as PTFE or others known in the art, in order to reduce friction. In one embodiment, the lace 23 comprises a stranded cable, such as a 7 by 7 strand cable manufactured of stainless steel. In order to reduce friction between the lace 23 and the guide members 50 through which the lace 23 slides, the outer surface of the lace 23 is preferably coated with a lubricious material, such as nylon or Teflon. In a preferred embodiment, the diameter of the lace 23 ranges from 0.024 inches to 0.060 inches and is preferably 0.032 inches. The lace 23 is desirably strong enough to withstand loads of at least 40 pounds and preferably at least about 90 pounds. In certain embodiments the lace is rated from about 100 pounds up to as high as 200 pounds or more.

As shown in FIG. 1, the tightening mechanism 25 is mounted to the orthopedic brace 20. Although the tightening mechanism 25 is shown mounted to a side-facing portion of the brace 20, it should be understood that the tightening mechanism 25 may be located at any of a variety of locations on the brace 20. Location of the tightening mechanisms 25 may be optimized in view of a variety of considerations, such as overall brace design as well as the intended use of the brace. The shape and overall volume of the tightening mechanism 25 can also be varied widely, depending upon the gear train design, and the desired use and location on the brace. A relatively low-profile tightening mechanism 25 is generally preferred. The mounted profile of the tightening mechanism 25 can be further reduced by recessing the tightening mechanism 25 into the outer surface 28 of the brace 20. In addition, like the guide members described above, the tightening mechanism may be configured to be removably attached to the brace to facilitate removal of the brace. For example, the housing 60 of the tightening mechanism 25 may be configured to be removably snapped into a recess in the brace.

In general, the tightening mechanism 25 comprises a control such as a lever, crank or knob, which can be manipulated to retract the lace 23. In addition, the tightening mechanism 25 preferably comprises a mechanism of release, such as a button or lever, for disengaging the tightening mechanism 25, to permit the lace 23 to be withdrawn freely. In some embodiments, the tightening mechanism is released by pulling outwards on the control. In some embodiments, an additional lock may be provided in the form of, for example, a button or lever, that must be actuated to allow the control to be, for example, pulled outwards to release the system.

The tightening mechanism 25 in the illustrated embodiment generally comprises a housing 60 and a circular knob 62 rotatably mounted thereto. The knob 62 may be rotated to wind the ends of the lace 23 into the housing 60, and thereby provide the final tension to the lace 23 to reduce the slack and provide the desired level of tightness. As the slack in the lace 23' reduces, the lace 23 pulls the guide members 50 and thereby the ends 32, 34 towards each other, tightening the upper and lower cuffs 10, 12 of the brace 20 around the wearer's leg. The knob 62 may also be rotated through the use of a tool or small motor attached to the knob 62. Examples of various tightening mechanisms suitable for this task are disclosed in greater detail in U.S. Patent Publication Nos. 2006-0156517 and 2007-0169378, incorporated herein by reference in their entireties.

The low friction relationship between the lace 23 and cable guides 50 greatly facilitate tightening and untightening the lacing system 22. Specifically, because the lace 23 and cable guides 50 are manufactured and/or coated with a low friction material, the lace 23 slides easily through the cable guides without catching. The lace 23 thus automatically distributes tension across its entire length, so that tightening pressure is evenly distributed along the length of the lacing zones. When the tension in the lace 23 is released by actuating the release lever (not shown) or by pulling outwards on the knob 62, the lace 23 slides easily through the cable guides 50 to release tension and evenly distribute any slack along the length of the lace.

The low friction relationship between the lace 23 and cable guides 50 also greatly facilitates a dynamic relationship between the different, tightened portions of the brace 20. For example, as a wearer's leg flexes during exercise and the thigh fills with blood and increases in volume, the upper portion of lacing system 22*a* can expand relative to the bottom portion of lacing system 22*a*. Thus, the low friction allows the orthopedic brace 20 to dynamically respond to varying volumes contained within the brace 20. In another embodiment, if the lower and upper cuffs 10, 12 were coupled to the wearer by a unitary lacing system 22, the tension along the entire brace 20 could be equilibrated by the lacing system 22.

In general, it is advantageous to design the lacing system such that it minimizes the possibility that portions of the system snag on clothing or other objects when in use. For example, the system may be configured to maintain a low profile when in the closed position. As mentioned above, one possibility is to recess the tightening mechanism into a portion of the brace. Another option that may be used alone or in combination with the recessed tightening mechanism is to provide a cover. In some embodiments, the cover includes a fabric or other flexible material that is fixedly attached to the brace or the housing of the tightening mechanism along at least one edge and is removably attached along one or more other edges by, for example, snaps, buttons or Velcro®. In some embodiments, the cover includes a more rigid portion made of, for example, plastic, and is attached to the brace with hinges that allow the cover to rotate off the brace to expose the tightening mechanism and to rotate back to cover the tightening mechanism. In some embodiments, a combination of hard and soft materials are used. In some embodiments, a cover is included that covers some or all of the lacing system including the laces, the lace guides, and the tightening mechanism.

In some embodiments, a shield may be provided that extends outward from the housing to cover at least a portion of the control of the tightening mechanism. Examples of shields to protect some or all of the control are discussed in greater detail in U.S. Patent Publication 2006-0156517 incorporated herein in its entirety.

Figure 2:
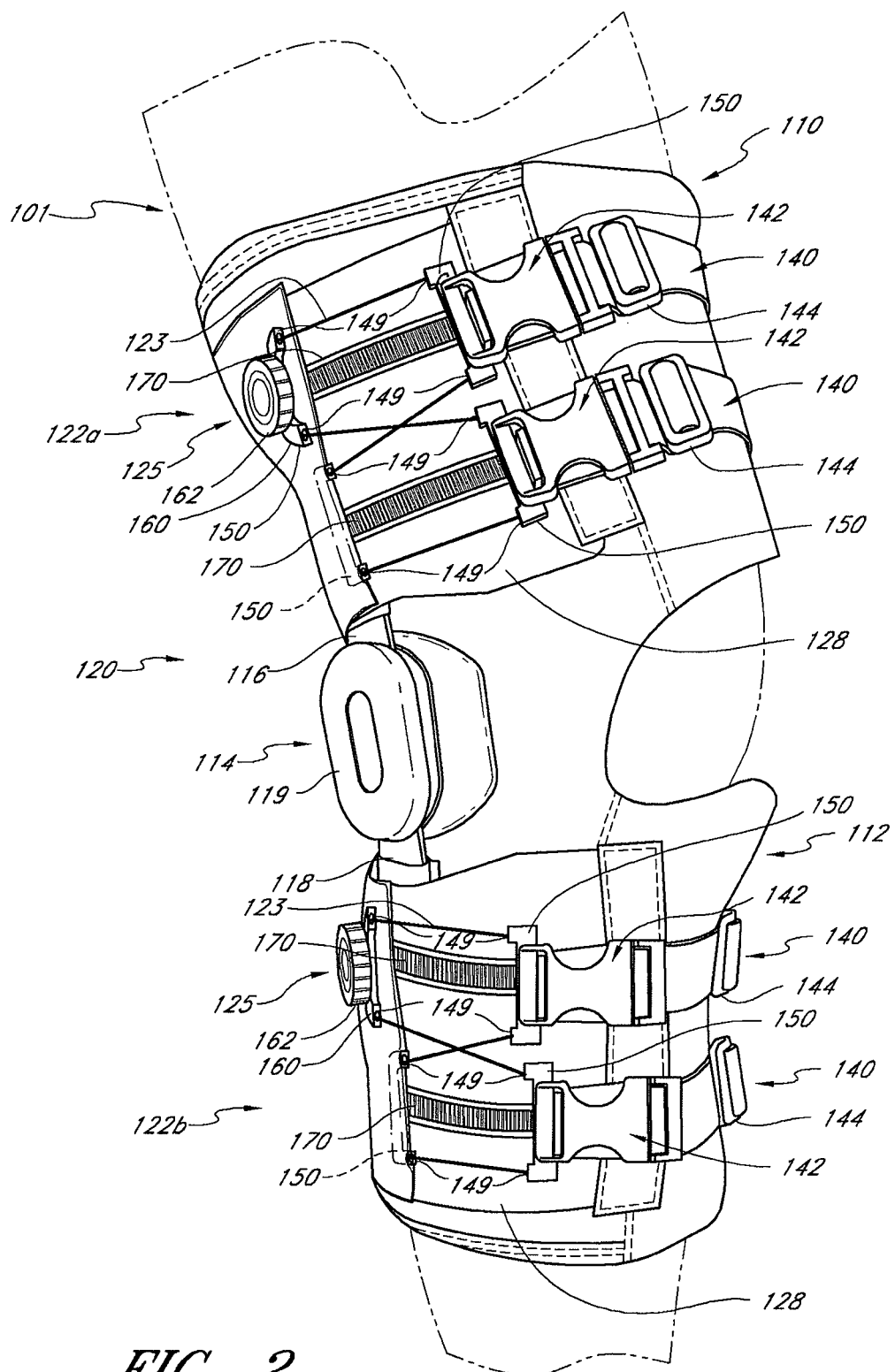
FIG. 2 is a perspective view of an orthopedic brace including a lacing system configured in accordance with one embodiment.
Figure 3:
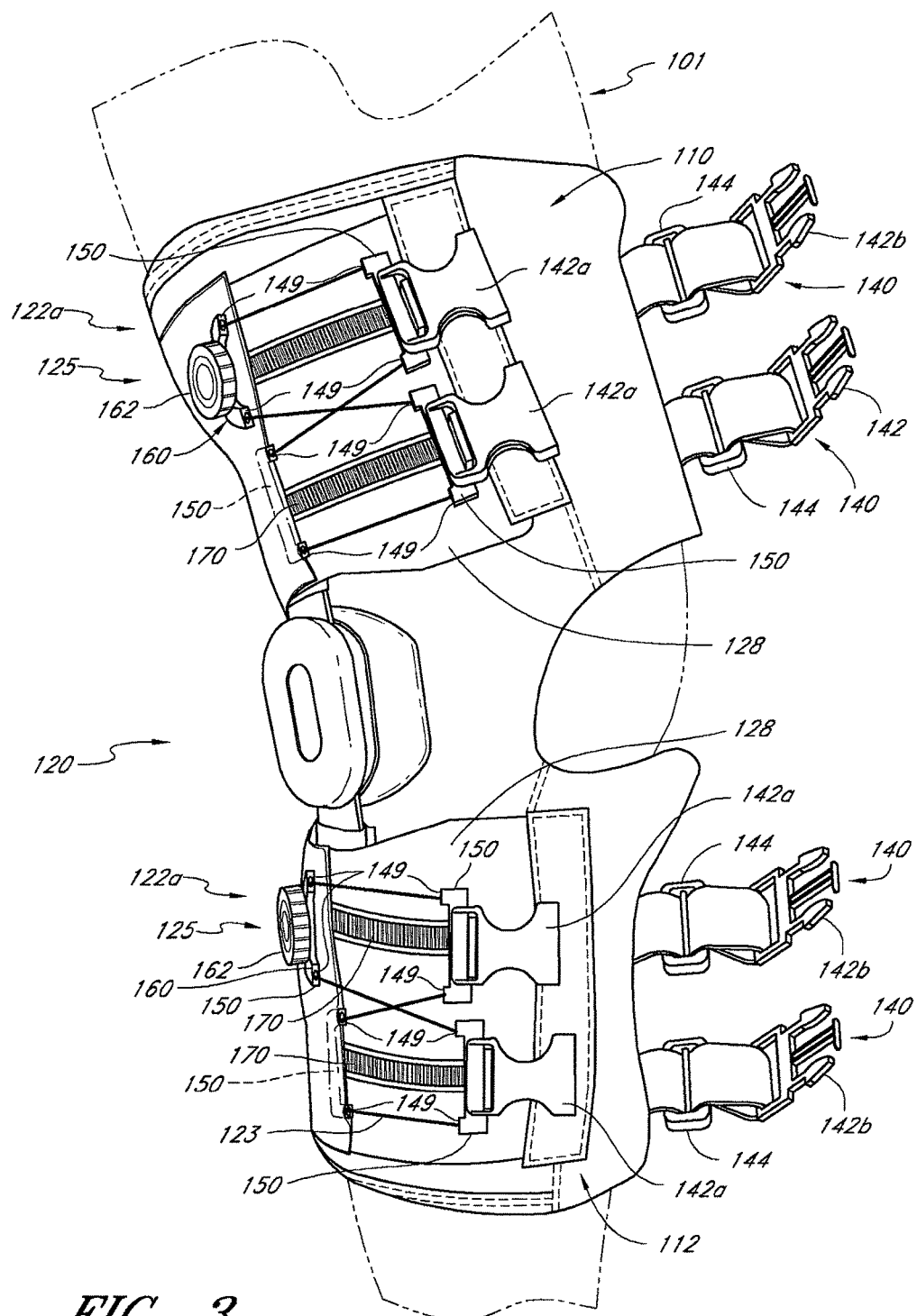
FIG. 3 is a perspective view of the orthopedic brace shown in FIG. 2 with a rough adjustment feature shown in an open configuration in accordance with one embodiment.

Referring now to FIGS. 2 and 3, another brace 120 is disclosed including a closure system 122 that includes rough adjustment features that permit further opening of the brace 120 to facilitate attachment of the brace 120 to a wearer's leg 101 while still providing the tightening mechanism 125 for final tightening. The upper cuff 110 is formed to fit the wearer's thigh and curves around the thing, generally conforming to the wearer's musculature. The lower cuff 112 is similar in construction to the upper cuff 110, and is formed to fit and curve around the wearer's calf. In the illustrated embodiments, the upper and lower cuffs include additional material connecting them near the knee joint, though in some embodiment they may be formed separately as shown, for example, in FIG. 1.

As described in the previous embodiment, the upper and lower cuffs 110, 112 may also be joined by at least one strut assembly 114, which may include an upper strut 116 and a lower strut 118 joined by a hinge assembly 119. The hinge assembly 119 preferably permits pivoting of the upper strut 116 relative to the lower strut 118, and associated bending of the wearer's knee.

In some embodiments, cuffs 110, 112 may be formed from single pieces of material that are wrapped around themselves, forming two ends (not shown) that are drawn towards each other and may overlap. The lace 123 may be tensioned to draw the ends past each other and thereby tighten the brace 120 about the wearer's limbs. Alternatively, the ends may include an initial attachment mechanism, such as Velcro® or the like (not shown), which may provide an initial joining of the ends around the limb prior to tensioning the system. In such a case, the lace 123 may be tensioned to draw the guide members 150 towards each other, compressing the cuffs around the limb rather than, or in addition to, drawing the ends together.

As shown in FIG. 2, in some embodiments each lacing or closure system 122 includes the lace 123 threaded in a crossing pattern along a generally side-facing portion of the brace 120, between two generally parallel rows of lace guides 150. In some embodiments, the guides 150 on the side of the tightening mechanism 125 may be integrally formed with the housing 160 of the tightening mechanism 125. The guides 150 positioned opposite the guides 150 on the side of the tightening mechanism 125 may be slidingly attached to the brace 120 on, for example, substantially parallel tracks 170 for reasons discussed below.

In some embodiments, it is advantageous to provide variable length retaining members 140 in order to better fit a wider variety of wearers' legs. In some embodiments, retaining members 140 are configured to be releasably engaged with guides 150 opposite the tightening mechanism 125. The engagement may be by way of a quick release mechanism 142, for example Fastex® buckles (shown), Velcro®, or other similar mechanisms known to those of skill in the art. As shown in greater detail in FIG. 3, each buckle 142 includes a female component 142*a* and a male component 142*b*. In some embodiments, the female component 142 a may be attached to the guide 150 while the male component 142*b* is attached to the retaining member, though the arrangement of components may be switched as needed. The opposite end of the retaining member 140 may be attached to the brace such that tension in the lacing system 122 causes tension on the retaining member 140 when the buckle 142 is engaged, thereby compressing the cuffs around the wearer's limb. In some embodiments, the retaining member 140 is attached on the same side of the brace 120 as the closure system 122 while in some embodiments it is attached to the side opposite the closure system 122.

Closure system 122 may include additional gross adjustment features in combination with the quick release mechanism 142 to provide a rough or gross adjustment of the closing pressure of the brace 120 prior to use of the tightening mechanism 125. For example, the closure system 122 may include ladder loops 144 which allow the retaining members 140 to be lengthened or shortened as needed. Though shown with two retaining members 140, as with the other embodiments disclosed herein in some embodiments the number of retaining members 140 may vary. In some embodiments, three, four, five, six or more retaining members 140 may be desirable.

As described above, each guide member 150 defines a pair of openings 149 that communicate with opposite ends of a lumen 154 extending therethrough. The openings 149 function as inlets/outlets for the lace 123.

In some embodiments, outer surfaces 128 of the brace 150 cuffs 110, 112 are relatively low friction in order to facilitate sliding of the guides 150 and the laces 123 over the surfaces 128 when the laces 123 are tightened. In some embodiments, the outer surface 128 is formed by adhering or stitching a flexible layer of nylon or polytetrafluoroethylene to the outer surface 128.

In the configuration shown in FIG. 2, the crossing pattern of the lacing system 122 may create an unbalanced tension on the guides 150 opposite the tightening mechanism 125. The force applied by the tightening mechanism 125 has two components, one which pulls the guides in a substantially parallel path and one that tends to move the guides 150 off that substantially parallel path and towards each other. To assist the travel of the guides 150 along that substantially parallel path, in some embodiments the guides 150 opposite the tightening mechanism 125 are attached to substantially parallel tracks 170. As tension is applied to the lacing system, the guides 150 are pulled along the tracks 170. It may be advantageous to keep the guides 150 along the substantially parallel paths to increase the effectiveness of the closure system 122. For example, if the guides 150 are pulled toward each other they may become tangled or bunched up which may cause discomfort to the wearer and may allow the brace 120 to slip down the wearer's leg 101.

FIG. 3 shows one embodiment of the brace 120 in a partially open configuration. The quick release buckles 142 have been disconnected leaving the guides 150 attached to the brace and releasing one end of the retaining member 140. To remove the brace 120, the user may then open the cuffs 110, 112 and slide the brace from the user's leg 101. Prior to releasing the buckles 142, the user may release tension in the closure system 122 by releasing the tightening mechanisms 125 by, for example, pulling outwards on the knobs 162. Alternatively, the user may release the tightening mechanisms 125 after releasing the buckles 142 to facilitate reattachment of the brace 120 by providing additional slack in the system without adjusting the retaining members 140 themselves.

Figure 4:
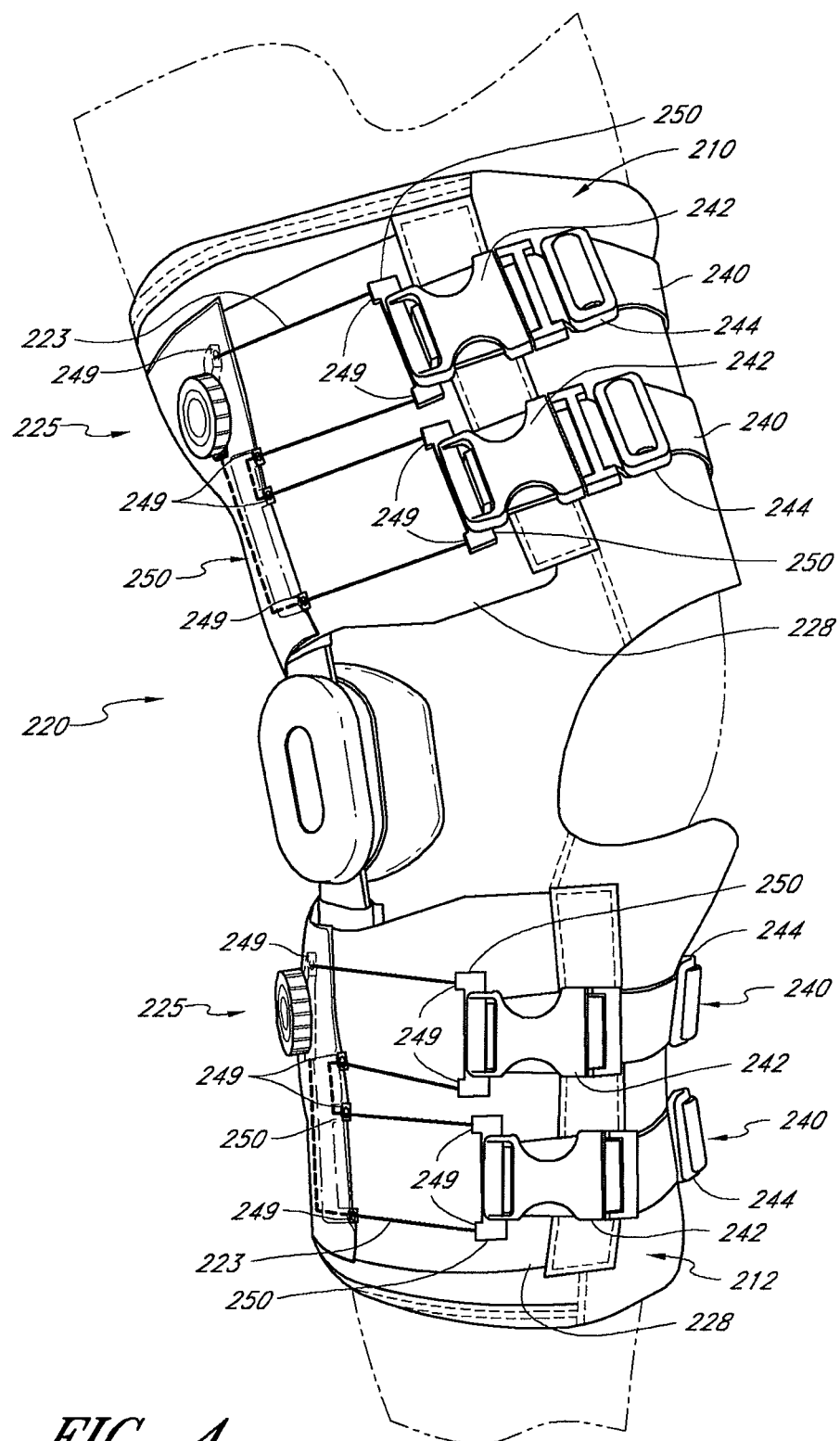
FIG. 4 is a perspective view of an orthopedic brace including a lacing system configured in accordance with one embodiment.

Referring now to FIG. 4, there is shown another embodiment of a brace 220 that is similar to brace 120 except that the lace does not form a crossing pattern in the lacing zone. Similar features have been labeled with similar reference numbers except the "1" has been replaced with a "2".

In some embodiments, the tightening mechanism 225 may include an integral guide member 250 with 4 openings 249. Alternatively the central two openings 249 could be formed into a separate guide member 250 and the outer two openings 249 could be formed integrally with the tightening member 225. In the illustrated embodiment, the bottom three openings 249 are formed in a single guide 250 and the top-most opening is integrally formed with the tightening mechanism 225. The lace 223 travels out the bottom of tightening mechanism 225, along the back of the guide 250 with the three bottom openings 249 and out the bottom-most opening 249. These configurations are by way of example as other configurations will be known to those of skill in the art.

By introducing a central pair of openings 249 on the side of the tightening mechanism 225, it is possible to configure the lace 223 such that it passes across the outer surface 228 of the brace 220 in a substantially parallel, uncrossed path. As such, the openings 249 are in a substantially parallel configuration. Such a configuration advantageously eliminates or substantially reduces the forces that tended to pull the guides 150 out of their substantially parallel paths. As such, in some embodiments it is possible to eliminate the tracks shown in the embodiment described above. Alternatively, the tracks may still be used to secure the guides 250 to the brace 220.

In general, the articles disclosed herein are advantageously designed to allow the user to move at least a portion of the closure system out of the way to facilitate insertion and removal of the limb or other body part from the article. Quick release mechanisms in combination with the tightening mechanisms permit quick, rough adjustment of the tightness of the article to the body while further permitting a more nuanced fit after attachment. In addition, the multiple closure systems allow a user to independently and selectively tension different parts of the articles to achieve a comfortable, yet effective fit to the body.

Figure 5:
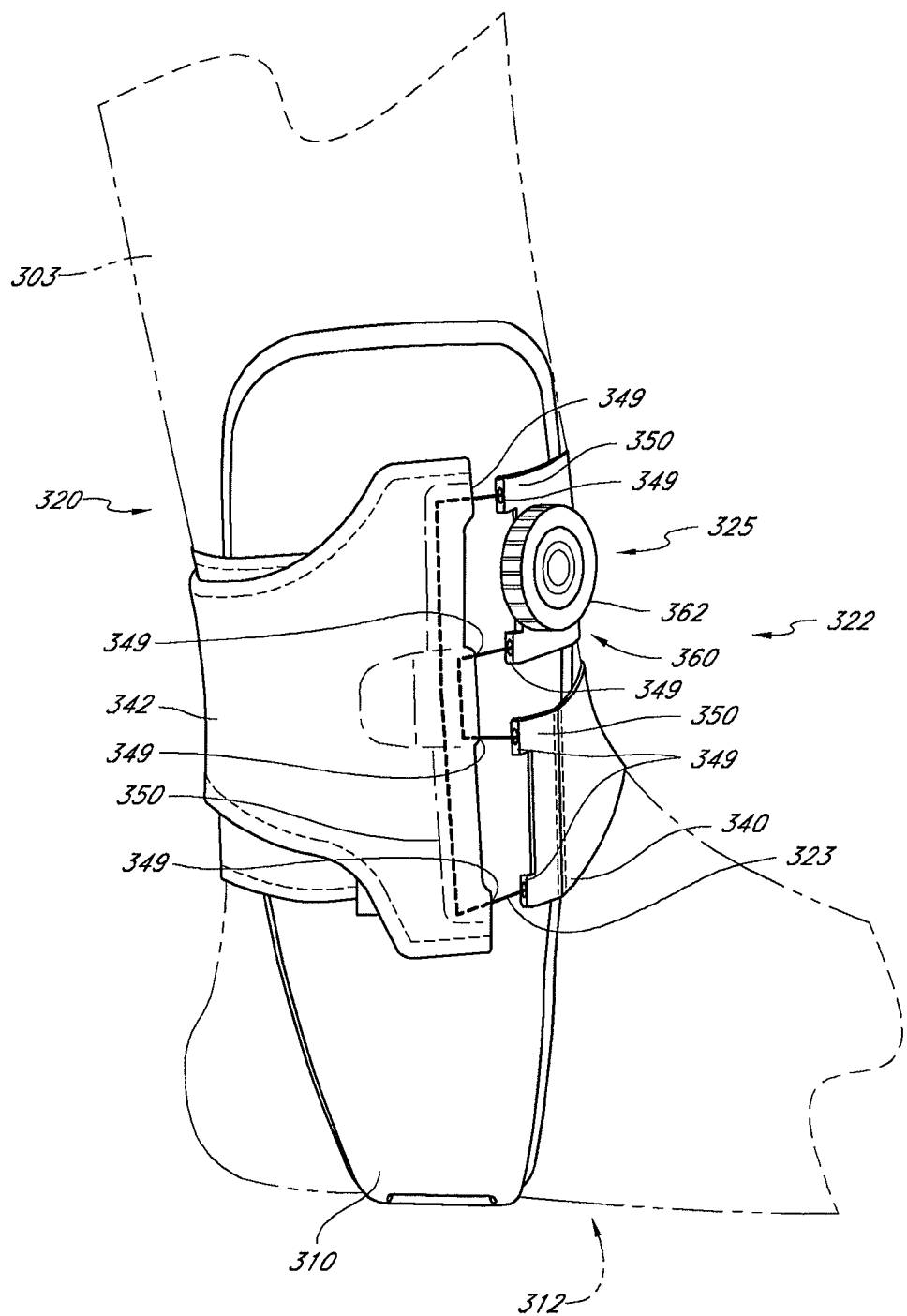
FIG. 5 is a side view of an orthopedic brace including a lacing system configured in accordance with one embodiment.
Figure 6:
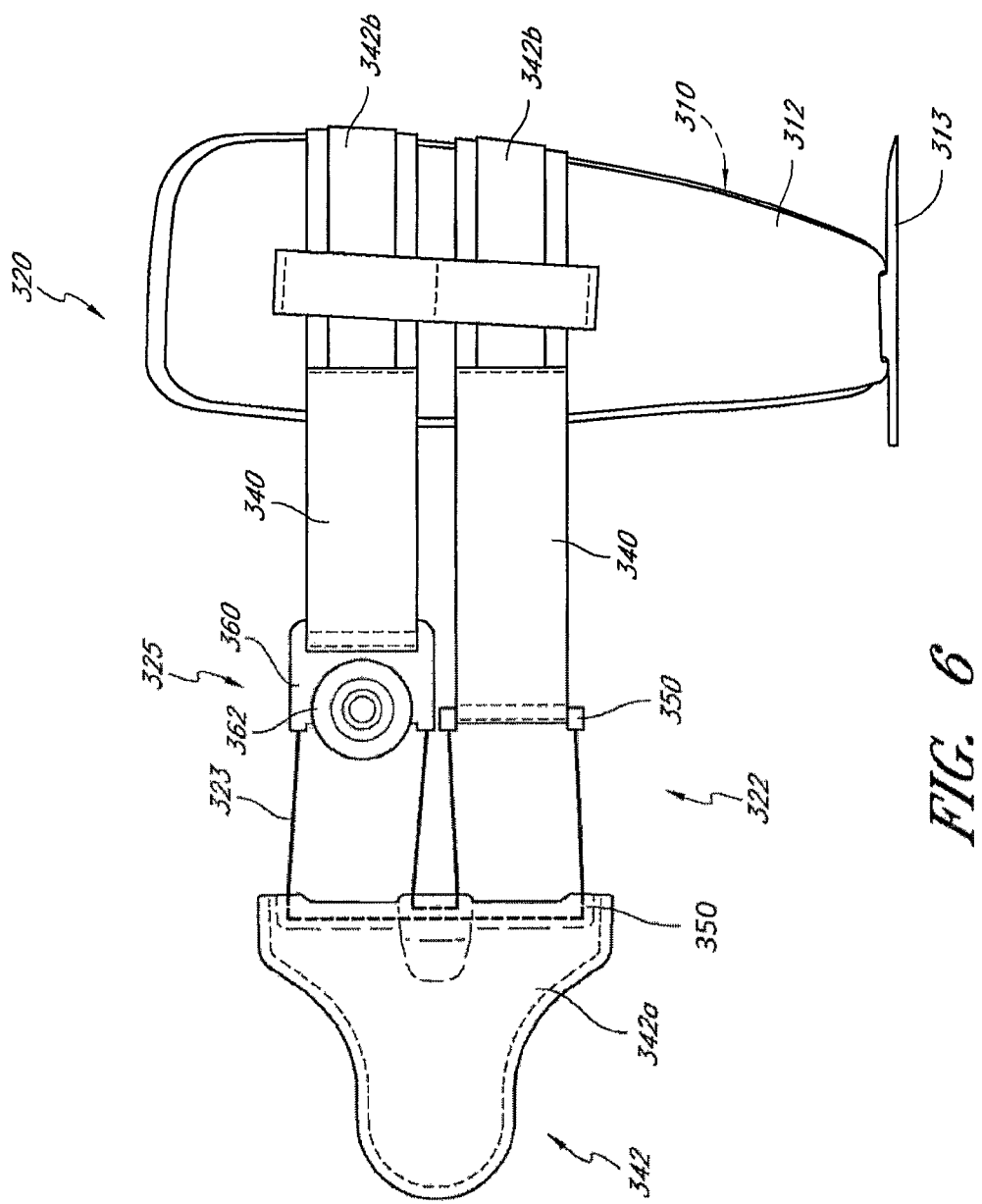
FIG. 6 is a side view of the orthopedic brace shown in FIG. 5 shown in an open configuration in accordance with one embodiment.

Referring now to FIGS. 5 and 6, there is shown a brace 320 for use with an ankle 303. In FIG. 5, the brace 320 is shown attached to the ankle 303. In FIG. 6, the brace 320 is shown in its open configuration. Brace 320 includes first and second ankle cuffs 310, 312 connected by connecting member 313 and configured to rest against the outside portions of a wearer's ankle 303. Ankle cuffs 310, 312 may include a rigid or substantially rigid member on the outside to provide stability to the ankle and a more resilient foam or air filled member on the inside to mold to and form a comfortable fitting against the ankle. Some embodiments of the brace 320 further include a closure system 322 including a tightening mechanism 325, guides 350, lace or cable 323 and a releasable retaining member 340.

In the illustrated embodiment, the brace is provided with a closure system 322 configured to adapt quickly and efficiently to differently sized ankles. In some embodiments, the guide 350 opposite the tightening mechanism 325 may be an unitary guide with four openings 349. These four openings 349 are preferably substantially parallel to the openings 349 on the side with the tightening mechanism 325 to provide a substantially parallel lace path for lace 323. Such a configuration provides the advantages discussed above with respect to brace 220, including eliminating or substantially reducing non-parallel tightening forces that may cause the retaining members to overlap and/or bunch up. In ankle braces, such a configuration is further advantageous as it may be difficult to include tracks or other mechanisms to control the path along which the guides travel given the need for the brace to accommodate a diverse set of differently sized limbs while providing a stabilizing brace that can be conveniently opened to accommodate the ankle. Embodiments of the brace disclosed herein can open wide enough to accommodate an injured ankle and provide both a rough and fine adjustment of the tightening pressure.

In the illustrated embodiment, Velcro® is used to provide a quick release mechanism 342 for the brace 320. After the ankle 303 is inserted into the brace 320, ankle cuffs 310, 312 are pressed against the wearer's ankle 303 and the retaining members 340 are wrapped around the ankle with the quick release members 342a, 342b combining to initially secure the brace 320 to the ankle. Final tightening is then accomplished by using tightening mechanism 325. In the illustrated embodiment, the knob 362 of tightening mechanism 325 is rotated to incrementally take up slack in lace 323 into housing 360. Tension in lace 323 may be released by pulling knob 362 away from housing 360 or by releasing the quick release member 342.

Figure 7:
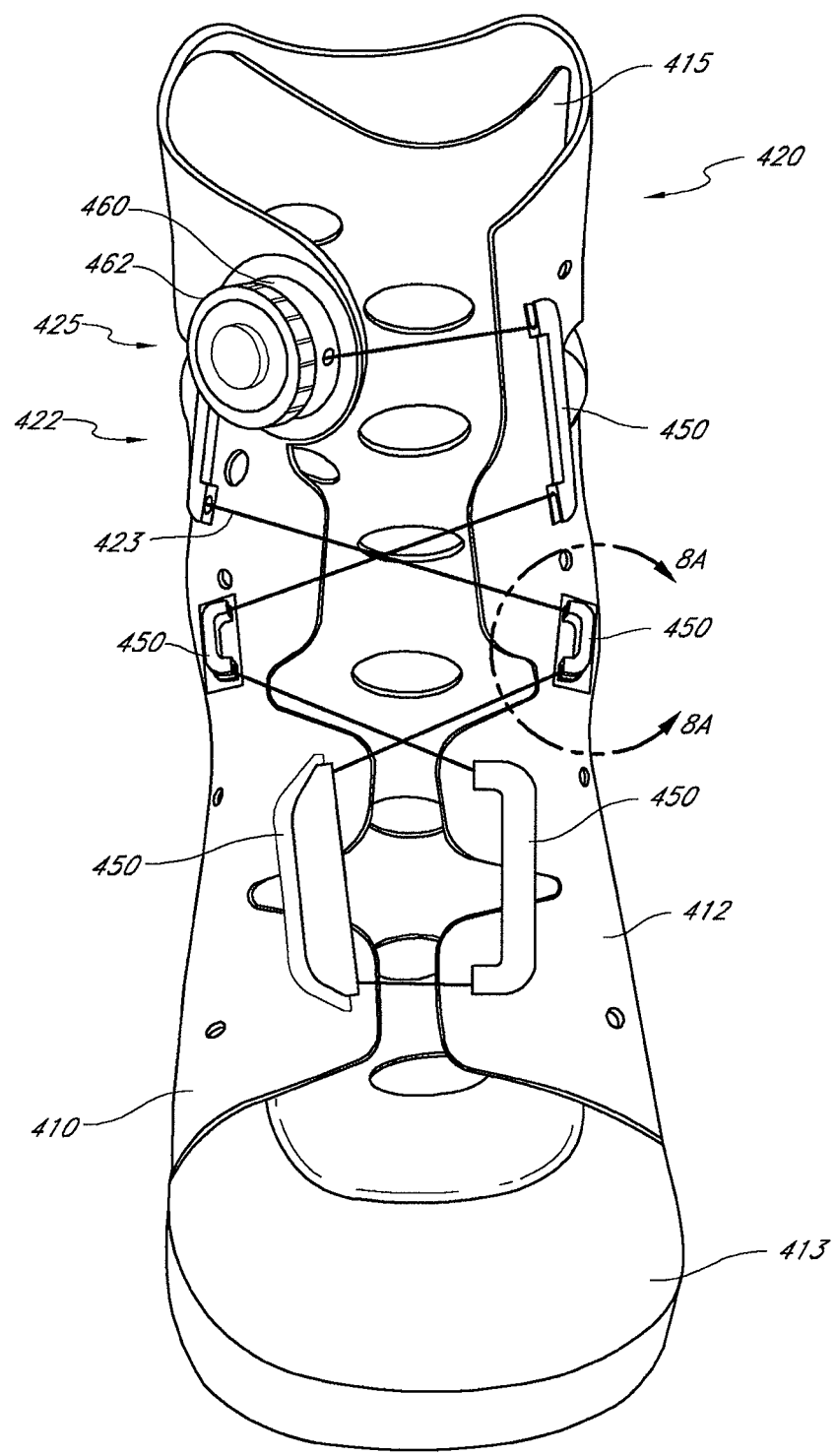
FIG. 7 is a front view of a foot/ankle brace including a lacing system configured in accordance with one embodiment.
Figure 8B:
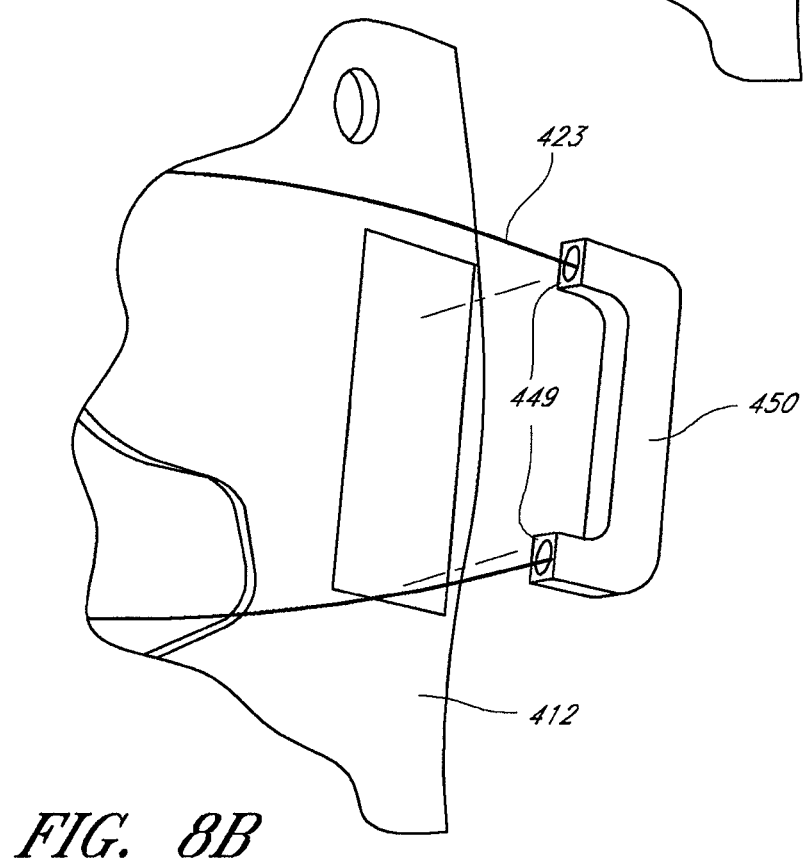
FIG. 8B is an alternative construction of the portion shown in FIG. 8A.
Figure 9:
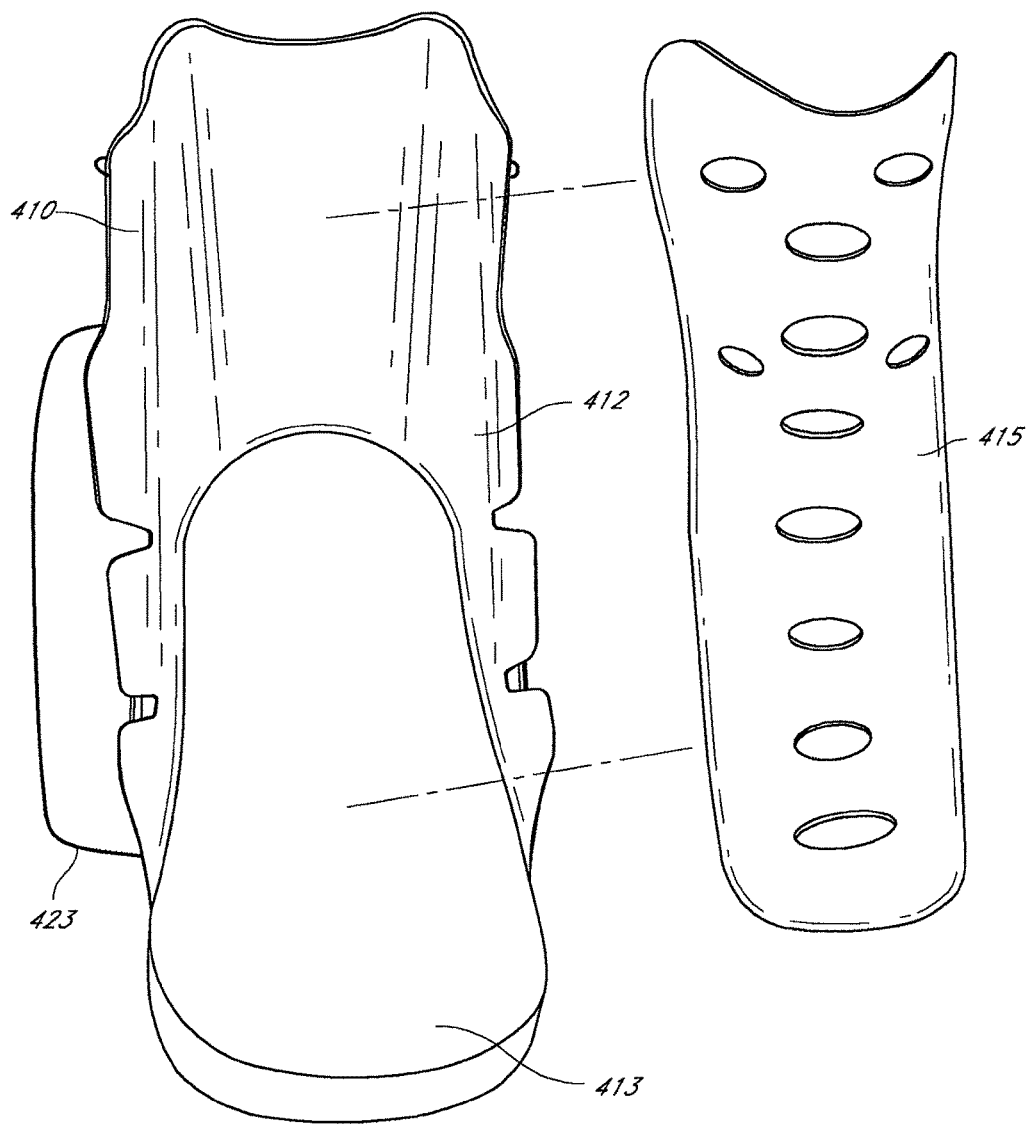
FIG. 9 is a front view of the foot/ankle brace shown in FIG. 7 shown in an open configuration in accordance with one embodiment.

Referring now to FIGS. 7 through 9, there is illustrated another embodiment including the present inventions incorporated into a foot brace 420. Some embodiments of the foot brace 420 include first and second sides 410, 412, a base or foot bed 413, a tongue 415, and a closure system 422. The first and second sides 410, 412 of the foot brace 420 may include a rigid or substantially rigid member on the outside to provide stability to the foot and ankle and a more resilient foam or air filled member on the inside to mold to and form a comfortable fitting against the foot and ankle. Similarly, tongue 415 may include a rigid or substantially rigid member on the outside to provide stability and protection and a softer, more resilient member on the inside to cushion the foot and ankle. The brace 420 is shown as a boot that would support both the foot and the ankle of a wearer. Other modifications of the brace may not include the ankle portion such that it only supports the foot of the wearer. Other modification may include a much taller portion that covers some or all of the lower leg and even up the upper leg of the wearer.

Advantageously, brace 420 is configured to facilitate the insertion and withdrawal of a wearer's foot and ankle from the brace. In particular, in some embodiments this is accomplished by providing a closure system 422 that includes quick release features allowing the opening between sides 410, 412 to be fully exposed and a tongue 415 that is fully removable from the opening.

In some embodiments, the lacing or closure system 422 includes the lace 423 threaded in a crossing pattern along a generally forward-facing portion of the brace 420, between two generally parallel rows of lace guides 450. As shown in FIG. 7 and in greater detail in FIG. 8A, one method of providing a quick release is to incorporate open ended guides 450 on the side of the boot opposite the tightening mechanism 425. To open the brace 420, the user releases tension on the lacing system 422 by, for example, pulling on the knob 462 of the tightening mechanism 425. With slack in the lace 423, the wearer can then remove the lace 423 from the guides 450 on the side opposite the tightening mechanism such that the lace 423 no longer spans the space between the sides 410, 412. With the lace 423 out of the way, the tongue 415 can be easily removed from the opening of the brace 420, giving the wearer an easy entry into the brace 420 with their appendage.

In some embodiments, the guides 450 placed in the middle of the brace 420 near the pivot point of the wearers' ankle include a shorter distance between the openings 449 than is used in the guides 450 closer to the toe of the brace 420 and higher up on the brace 420. This shorter distance increases the closing force in the area around the pivot point to help lock the ankle and foot into the brace 420. In some embodiments, it is advantageous to include one or more open backed guides 450 on the tightening mechanism 425 side of the brace 420 to increase the amount of slack lace available to the user when the closure system 422 is open. One example of such a configuration is shown in FIG. 7.

FIG. 8B shows an alternative to the open backed guide design described above. The removable enclosed guide 450 shown in FIG. 8B may be used in lieu of one or more of the open backed guides shown in FIGS. 7 and 8A. Removable guide 450 may be attached to the brace 420 in one or more ways known to those of skill in the art. For example, hooks may be incorporated on the portion of the guide which contacts the brace and may be configured to engage mating holes on the brace. Alternatively, hooks may be formed on the boot and complementary holes formed on the guide. Other removable snaps, rivets and fasteners may be used as will be known to those of skill in the art.

In some embodiments, tongue 415 is completely removable from brace 420 as shown in FIG. 9. In some embodiments, tongue 415 may be configured such that it allows complete opening of the brace 420 while not being completely separated from brace 420. For example, tongue 415 may include guides (not shown) in one or more locations that guide the lace 423 across the tongue 415 when the brace 420 is closed and maintain a connection between the tongue 415 and the brace 420 when the brace 420 is in its open configuration.

Figure 10:
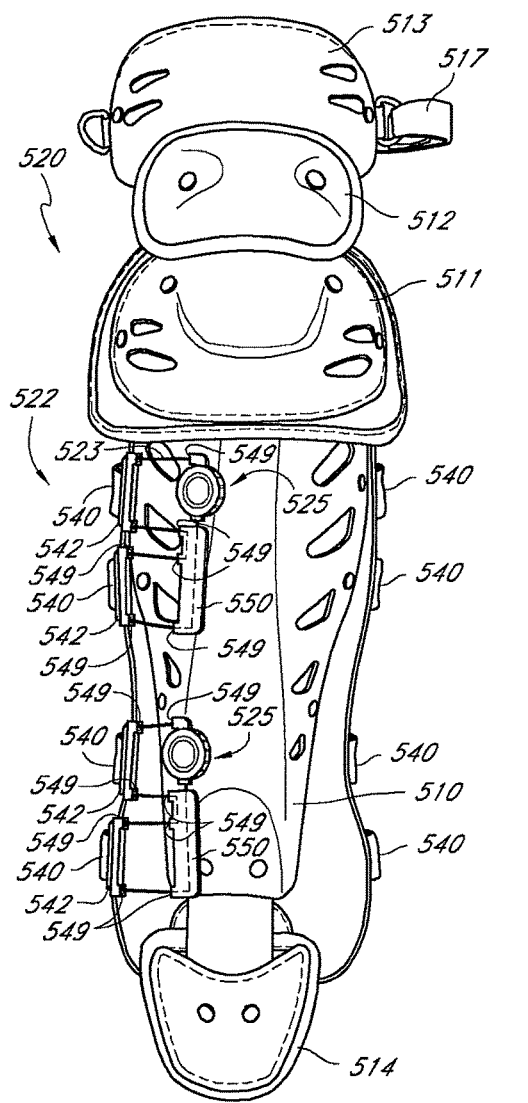
FIG. 10 is a front view of an article of protective wear including a closure system configured in accordance with one embodiment.
Figure 11:
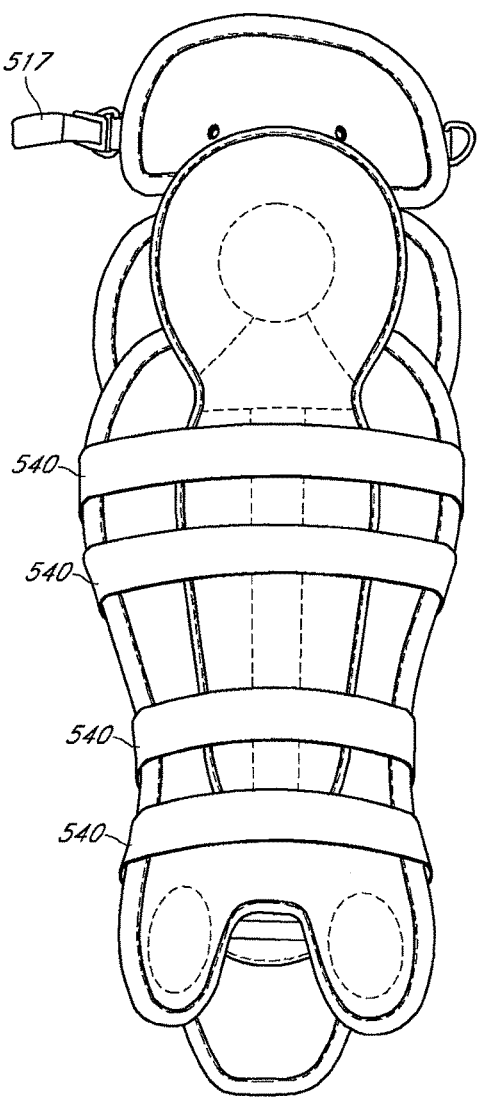
FIG. 11 is a rear view of the embodiment shown in FIG. 10.

Referring now to FIGS. 10 and 11, an article of protective wear 520 is shown prepared in accordance with the present inventions. The illustrated example is a shin guard 520 configured for use in, for example, baseball or softball, and generally comprises one or more protective members 510, 511, 512, 513, 514 that are tightened around a wearer's leg (not shown) using a closure or lacing configuration comprising one or more lacing systems 522.

In the illustrated embodiment, several protective members are joined to form the shin guard 520. Main portion 510 is configured to protect some or all of the shin of the wearer. Upper portions 511, 512, 513 are movably connected to main portion 510 and are configured to protect the knee and lower thigh of wearer. Lower portion 514 may be configured to protect the wearer's ankle and a portion of the foot. In some embodiments, uppermost portion 513 includes an elastic strap to 517 to keep it movably fixed to the wearer's thigh. In some embodiments, uppermost portion 513 may include a lacing system 522 as disclosed herein.

The lacing system 522 used in the shin guard 520 may include one or more of the variations described in detail above. In some embodiments, lacing system 522 includes a tightening member 525 configured for attachment to the main portion 510 of the guard 520. The lacing zone may be created by one or more pairs of lace guides 550 and a lace 523 extending therebetween. In some embodiments, quick release members 542 are included to facilitate entry and exit into the guard 520. In some embodiments, retaining members 540 extend around the wearer's leg and are connected to the lace guides 550 by one or more quick release members 542.

Although these inventions have been disclosed in the context of certain embodiments and examples, it will be understood by those skilled in the art that the inventions extend beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. For example, the knob covers disclosed with respect to the first embodiment could be used with any of the embodiments disclosed herein. Accordingly, it should be understood that various features and aspects of the disclosed embodiments can be combined with or substituted for one another in order to form varying modes of the disclosed invention. Thus, it is intended that the scope of the inventions herein disclosed should not be limited by the particular disclosed embodiments described above.

What is claimed is:

1. A closure system for use with a brace configured to be worn on a body or limb, the brace having first and second opposing sides, the closure system comprising:
   a first lace guide that is removably coupled with the first side of the brace;
   one or more second lace guides generally opposing the first lace guide;
   a lace extending between the first lace guide and the one or more second lace guides;
   a rotatable tightening mechanism configured to apply tension to the lace; and
   a single quick release member configured to remove the first lace guide from the first side of the brace; wherein:
   the first lace guide is a unitary guide comprising four openings;
   the unitary guide comprises a first channel extending between a first pair of openings and a second channel extending between a second pair of openings; and
   the first and second channels are arranged so that the second channel is positioned laterally outward of the first channel and so that the first pair of openings is positioned between the second pair of openings; and
   the lace is positioned within the first and second channels.

2. The closure system of claim 1, further comprising at least one retaining member that couples the one or more second lace guides to the brace.

3. The closure system of claim 2, wherein the at least one retaining member comprises a first end coupled to the brace and a second end coupled to the one or more second lace guides.

4. The closure system of claim 3, wherein the first end of the at least one retaining member is coupled to the second side of the brace.

5. The closure system of claim 3, wherein the closure system is configured such that tightening the lace with the rotatable tightening mechanism draws the first lace guide towards the second end of the at least one retaining member.

6. The closure system of claim 2, wherein the rotatable tightening mechanism is on the at least one retaining member.

7. The closure system of claim 1, wherein one of the one or more second lace guides is integrally formed with a housing of the rotatable tightening mechanism.

8. The closure system of claim 1, wherein the lace extends across substantially parallel lace paths between the first lace guide and the one or more second lace guides.

9. The closure system of claim 1, wherein the quick release member comprises hook and loop fastener components.

10. The closure system of claim 1, wherein the one or more second lace guides comprise a plurality of second lace guides formed on separate lace guides.

11. The closure system of claim 1, wherein the quick release member is configured to provide a rough adjustment of a tightness of the brace, and wherein the rotatable tightening mechanism is configured to provide a fine adjustment of the tightness of the brace.

12. The closure system of claim 1, wherein the brace is configured for use with a foot, ankle, or knee.

13. The closure system of claim 1, wherein the brace comprises a substantially rigid member configured to provide stability, and a resilient member on an inside configured to mold to the body or limb.

14. The closure system of claim 1, configured such that rotation of the rotatable tightening mechanism to apply tension to the lace advances the first lace guide and the one or more second lace guides towards each other.

15. The closure system of claim 1, wherein the one or more second lace guides comprises a plurality of second lace guides generally opposing the first lace guide, and wherein a single lace extends between the first lace guide and the plurality of second lace guides.

16. A closure system for use with a brace configured to be worn on a body or limb, the brace having first and second opposing sides, the closure system comprising:
    a first unitary lace guide comprising four openings, the first unitary lace guide having an inner lace channel that extends between a first pair of openings and an outer lace channel that extends between a second pair of openings, the first unitary lace guide also having an attachment member that removably attaches the first unitary lace guide to the brace to removably couple the inner lace channel and the outer lace channel on the first side of the brace;
    one or more second lace guides generally opposing the inner lace channel and the outer lace channel of the first unitary lace guide;
    a lace extending between the inner lace channel and the outer lace channel of the first unitary lace guide and the one or more second lace guides; and
    a rotatable tightening mechanism configured to apply tension to the lace;
    wherein the attachment member is detachable from the brace so that the first unitary lace guide and the inner lace channel and the outer lace channel are removable from the first side of the brace;
    wherein a longitudinal length of the outer lace channel is greater than a longitudinal length of the inner lace channel such that the outer lace channel is positioned laterally outward of the inner lace channel and the inner lace channel is disposed between opposing ends of the outer lace channel with the first pair of openings positioned between the second pair of openings; and
    wherein the lace is positioned within the inner lace channel and the outer lace channel.

17. The closure system of claim 16, further comprising at least one retaining member that couples the one or more second lace guides to the brace.

18. The closure system of claim 17, wherein the at least one retaining member comprises a first end coupled to the brace and a second end coupled to the one or more second lace guides.

19. The closure system of claim 18, wherein the first end of the at least one retaining member is coupled to the second side of the brace.

20. The closure system of claim 18, wherein the closure system is configured such that tightening the lace with the rotatable tightening mechanism draws the first unitary lace guide towards the second end of the at least one retaining member.

21. The closure system of claim 17, wherein the rotatable tightening mechanism is on the at least one retaining member.

22. The closure system of claim 16, wherein one of the one or more second lace guides is integrally formed with a housing of the rotatable tightening mechanism.

23. The closure system of claim 16, wherein the lace extends across substantially parallel lace paths between the inner lace channel and the outer lace channel of the first unitary lace guide and the one or more second lace guides.

24. The closure system of claim 16, wherein the attachment member comprises a hook and loop fastener component configured to engage a corresponding hook and loop fastener component on the brace.

25. The closure system of claim 16, wherein the one or more second lace guides comprise a plurality of separate lace guides.

26. The closure system of claim 16, wherein the attachment member is configured to provide a rough adjustment of a tightness of the brace, and wherein the rotatable tightening mechanism is configured to provide a fine adjustment of the tightness of the brace.

27. The closure system of claim 16, wherein the brace is configured for use with a foot, ankle, or knee.

28. The closure system of claim 16, wherein the brace comprises a substantially rigid member configured to provide stability, and a resilient member on an inside configured to mold to the body or limb.

29. The closure system of claim 16, wherein the rotatable tightening mechanism is configured such that rotation of the rotatable tightening mechanism advances the first unitary lace guide and the one or more second lace guides towards each other.

30. The closure system of claim 16, wherein the one or more second lace guides comprises a plurality of lace guides generally opposing the first unitary lace guide, and wherein a single lace extends between the first unitary lace guide and the plurality of lace guides.

* * * * *